(12) United States Patent
Lee et al.

(10) Patent No.: US 8,012,925 B2
(45) Date of Patent: Sep. 6, 2011

(54) AGENT FOR INDUCING APOPTOSIS COMPRISING MSX1 OR A GENE ENCODING THE SAME AS AN ACTIVE INGREDIENT

(75) Inventors: Je-Ho Lee, Seoul (KR); Kyoungsook Park, Seoul (KR)

(73) Assignee: Sungkyunkwan University Foundation for Corporate Collaboration (KR)

( * ) Notice: Subject to any disclaimer, the term of this patent is extended or adjusted under 35 U.S.C. 154(b) by 75 days.

(21) Appl. No.: 12/343,104

(22) Filed: Dec. 23, 2008

(65) Prior Publication Data

US 2010/0016222 A1     Jan. 21, 2010

Related U.S. Application Data

(63) Continuation of application No. 11/344,633, filed on Jan. 30, 2006, now abandoned.

(30) Foreign Application Priority Data

Jul. 22, 2005   (KR) ............................ 10-2005-66541

(51) Int. Cl.
*A01N 37/18*   (2006.01)
(52) U.S. Cl. ........................................ 514/1.1; 530/350
(58) Field of Classification Search .................. None
See application file for complete search history.

(56) References Cited

U.S. PATENT DOCUMENTS 7,371,835 B2   5/2008   Nakamura et al.
2007/0021337 A1   1/2007   Lee et al.

FOREIGN PATENT DOCUMENTS

WO   WO 02/40717   5/2002

OTHER PUBLICATIONS

Freshney, Culture of Animal Cells, A Manual of Basic Technique, Alan R. Liss, Inc., 1983, New York, p4.*
Dermer, Bio/Technology, 1994, 12:320.*
Gura, Science, 1997, 278:1041-1042.*
Johnson and Tracey, 'Peptide and Protein Drug Delivery', In: Encyclopedia of Controlled Drug Delivery, vol. 2, 1999, pp. 816-833.*
Burgess et al ( J of Cell Bio. 111:2129-2138, 1990.*
Bowie et al, Science, 1990, 257:1306-1310.*
Lazar et al, Molecular and Cellular Biology, 1988, 8:1247-1252.*
Ashcroft, et al. "Regulation of p53 Stability", Oncogene, 18:7637-7643 (1999).
Bendall, et al. "Roles for Msx and Dlx Homeoproteins in Vertebrate Development", Gene, 247:17-31 (2000).
Butz, et al. "Induction of Apoptosis in Human Papillomavirus-Positive Cancer Cells by peptide Aptamers Targeting the Viral E6 Oncoprotein", PNAS USA 97(12):6693-6697 (2000).
Hengstermann, et al. "Complete Switch from Mdm2 to Human Papillomavirus E6-Mediated Degradation of p53 in Cervical Cancer Cells", PNAS USA 98(3):1218-1233 (2001).

Oda, et al. "P53AIP1, A Potential Mediator of p53-Dependent Apoptosis, and Its Regulation by Ser-46-Phosphoylated p53," Cell 102:849-862 (2000).
Park, et al. "Homeobox Msx 1 Interacts with p53 Tumor Supressor and Inhibits Tumor Growth by Inducing Apoptosis", Cancer Res 65(3):749-757 (2005).
U.S. Appl. No. 12/107,492, Muramatsu (Apr. 22, 2008).
U.S. Appl. No. 12/253,418, Lee, et al. (Oct. 17, 2008).
Gura (1997, Science 278:1041-1042).
Johnson, et al., 'Peptide and Protein Drug Delivery', In: Encyclopedia of Controlled Drug Delivery, vol. 2, 1999, pp. 816-833.
Joliet, et al. "Advanced Drug Delivery Reviews", 60:608-613 (2008).
Marshall, "Gene Therapy's Growing Pains," Science, Aug. 1995, pp. 1050-1055, vol. 269.
Rubanyi, "The Future of Human Gene Therapy," Molecular Aspects of Medicine, 2001, vol. 22, pp. 113-142.
Takakura et al., "Development of Gene Drug Delivery Systems Based on Pharmacokinetic Studies," European Journal of Pharmaceutical Sciences, 2001, 13, pp. 71-76.
Verma et al., "Gene Therapy—Promises, Problems and Prospects," Nature, Sep. 18, 1997, pp. 239-242, vol. 389.
Official Action for U.S. Appl. No. 12/253,418, mailed Nov. 12, 2010.
Amsellem et al. "Ex vivo expansion of human hematopoietic stem cells by direct delivery of the HOXB4 homeoprotein," Nature Medicine, Nov. 2003, vol. 9, No. 11, pp. 1423-1427.
Jacob et al. "Suppression of pancreatic tumor growth in the liver by systemic administration of the TRAIL gene driven by the hTERT promoter." Cancer Gene Therapy, Feb. 2005, vol. 12, No. 2, pp. 109-115.
Joliot et al. "Transduction peptides: from technology to physiology," Nature Cell Biology, Mar. 2004, vol. 6, No. 3, pp. 189-196.
Lebedeva et al. "Tumor Suppression and Therapy Sensitization of Localized and Metastitic Breast Cancer by Adenovirus p53." Human Gene Therapy, May 1, 2001, vol. 12, pp. 763-772. Muruve et al. "Adenovirus-Mediated Expression of Fas Ligand Induces Hepatic Apoptosis after Systemic Administration and Apoptosis of Ex Vivo-Infected Pancreatic Islet Allografts and Isografts." Human Gene Therapy, May 20, 1997, vol. 8, pp. 955-963.
Tada et al. "Systemic IFN-β gene therapy results in long-term survival in mice with established colorectal liver metastases." The Journal of Clinical Investigation, Jul. 1, 2001, vol. 108, No. 1, pp. 83-95.

* cited by examiner

*Primary Examiner* — Misook Yu
*Assistant Examiner* — Mark Halvorson
(74) *Attorney, Agent, or Firm* — Sheridan Ross P.C.

(57) ABSTRACT

The present invention relates to a novel use of Msx1 protein or a nucleotide encoding the same for inducing apoptosis. The Msx1 of the present invention induces apoptosis through direct interaction with p53 via a homeodomain and such interaction leads to increased stability, and/or nuclear localization of p53 in cells. The Msx1 or homeodomain thereof can be effectively used for the treatment of tumors, in which wild-type p53 protein has lost its function by some mechanism that inactivates p53 proteins.

12 Claims, 16 Drawing Sheets

Control vector    full Msx1 vector

SEQUENCE LISTING

```
<160> NUMBER OF SEQ ID NOS: 4

<210> SEQ ID NO 1
<211> LENGTH: 370
<212> TYPE: PRT
<213> ORGANISM: Homo sapiens

<400> SEQUENCE: 1

Cys Leu Arg Gly Gly Ser Asp Arg Arg Pro Gly Pro Ala Arg Arg Ser
 1               5                  10                  15

Trp Pro Ala Gly Glu Gly Arg Glu Ala Arg Ala Gly Gly Ser Ala Arg
            20                  25                  30

Pro Gly Pro Arg Ala Leu Ala Glu Ala Gly Arg Ala Pro Ser Pro Pro
        35                  40                  45
```

```
Gly Ala His Ala Arg Arg Leu Ala Ser Ala Ala Glu Gly Gly Ala
         50                  55                  60
Arg Leu Cys Met Ala Pro Ala Ala Asp Met Thr Ser Leu Pro Leu Gly
 65                  70                  75                  80
Val Lys Val Glu Asp Ser Ala Phe Gly Lys Pro Ala Gly Gly Ala
                 85                  90                  95
Gly Gln Ala Pro Ser Ala Ala Ala Thr Ala Ala Met Gly Ala
                100                 105                 110
Asp Glu Glu Gly Ala Lys Pro Lys Val Ser Pro Ser Leu Leu Pro Phe
                115                 120                 125
Ser Val Glu Ala Leu Met Ala Asp His Arg Lys Pro Gly Ala Lys Glu
130                 135                 140
Ser Ala Leu Ala Pro Ser Glu Gly Val Gln Ala Gly Gly Ser Ala
145                 150                 155                 160
Gln Pro Leu Gly Val Pro Pro Gly Ser Leu Gly Ala Pro Asp Ala Pro
                165                 170                 175
Ser Ser Pro Arg Pro Leu Gly His Phe Ser Val Gly Gly Leu Leu Lys
                180                 185                 190
Leu Pro Glu Asp Ala Leu Val Lys Ala Glu Ser Pro Glu Lys Pro Glu
                195                 200                 205
Arg Thr Pro Trp Met Gln Ser Pro Arg Phe Ser Pro Pro Ala Arg
210                 215                 220
Arg Leu Ser Pro Pro Ala Cys Thr Leu Arg Lys His Lys Thr Asn Arg
225                 230                 235                 240
Lys Pro Arg Thr Pro Phe Thr Thr Ala Gln Leu Leu Ala Leu Glu Arg
                245                 250                 255
Lys Phe Arg Gln Lys Gln Tyr Leu Ser Ile Ala Glu Arg Ala Glu Phe
                260                 265                 270
Ser Ser Ser Leu Ser Leu Thr Glu Thr Gln Val Lys Ile Trp Phe Gln
                275                 280                 285
Asn Arg Arg Ala Lys Ala Lys Arg Leu Gln Glu Ala Glu Leu Glu Lys
                290                 295                 300
Leu Lys Met Ala Ala Lys Pro Met Leu Pro Ala Ala Phe Gly Leu
305                 310                 315                 320
Ser Phe Pro Leu Gly Gly Pro Ala Ala Val Ala Ala Ala Gly Ala
                325                 330                 335
Ser Leu Tyr Gly Ala Ser Gly Pro Phe Gln Arg Ala Ala Leu Pro Val
                340                 345                 350
Ala Pro Val Gly Leu Tyr Thr Ala His Val Gly Tyr Ser Met Tyr His
                355                 360                 365
Leu Thr
370

<210> SEQ ID NO 2
<211> LENGTH: 1546
<212> TYPE: DNA
<213> ORGANISM: Homo sapiens

<400> SEQUENCE: 2
ctgcctgcgc ggcggcagcg accggaggcc aggcccagca cgccggagct ggcctgctgg      60
ggaggggcgg gaggcgcgcg cgggagggtc cgcccggcca gggcccgggg cgctcgcaga     120
ggccggccgc gctcccagcc cgcccggagc ccatgcccgg cggctggcca gtgctgcggc     180
agaagggggg gccggctct gcatggcccc ggctgctgac atgacttctt tgccactcgg     240
tgtcaaagtg gaggactccg ccttcggcaa gccggcgggg ggaggcgcgg gccaggcccc     300
```

```
cagcgccgcc gcggccacgg cagccgccat gggcgcggac gaggaggggg ccaagcccaa      360
agtgtcccct tcgctcctgc ccttcagcgt ggaggcgctc atggccgacc acaggaagcc      420
gggggccaag gagagcgccc tggcgccctc cgagggcgtg caggcggcgg gtggctcggc      480
gcagccactg ggcgtcccgc cggggtcgct gggagccccg gacgcgccct cttcgccgcg      540
gccgctcggc catttctcgg tggggggact cctcaagctg ccagaagatg cgctcgtcaa      600
agccgagagc cccgagaagc ccgagaggac cccgtggatg cagagccccc gcttctcccc      660
gccgccggcc aggcggctga ccccccagc  ctgcaccctc cgcaaacaca agacgaaccg      720
taagccgcgg acgcccttca ccaccgcgca gctgctggcg ctggagcgca agttccgcca      780
gaagcagtac ctgtccatcg ccgagcgcgc ggagttctcc agctcgctca gcctcactga      840
gacgcaggtg aagatatggt tccagaaccg ccgcgccaag gcaaagagac tacaagaggc      900
agagctggag aagctgaaga tggccgccaa gcccatgctg ccaccggctg ccttcggcct      960
ctccttccct ctcggcggcc ccgcagctgt agcggccgcg gcgggtgcct cgctctacgg     1020
tgcctctggc cccttccagc gcgccgcgct gcctgtggcg cccgtgggac tctacacggc     1080
ccatgtgggc tacagcatgt accacctgac atagagggtc caggtcgcc  cacctgtggg     1140 ccagccgatt cctccagccc tggtgctgta ccccgacgt  gctcccctgc tcggcaccgc     1200
cagccgcctt ccctttaacc ctcacactgc tccagtttca cctctttgct ccctgagttc     1260
actctccgaa gtctgatccc tgccaaaaag tggctggaag agtcccttag tactcttcta     1320
gcatttagat ctacactctc gagttaaaga tggggaaact gagggcagag aggttaacag     1380
atttatctag ggtccccagc agaattgaca gttgaacaga gctagaggcc atgtctcctg     1440
catagctttt ccctgtcctg acaccaggca agaaagcgc  agagaaatcg gtgtctgacg     1500
attttggaaa tgagaacaat ctcaaaaaaa aaaaaaaaa  aaaaaa                    1546
```

<210> SEQ ID NO 3
<211> LENGTH: 31
<212> TYPE: DNA
<213> ORGANISM: Artificial Sequence
<220> FEATURE:
<223> OTHER INFORMATION: Forward primer for amplifying DNA encoding
      homeodomain of Msx1

<400> SEQUENCE: 3
attgtcgaca accggcaagc ccaggacgcc t                                      31

<210> SEQ ID NO 4
<211> LENGTH: 29
<212> TYPE: DNA
<213> ORGANISM: Artificial Sequence
<220> FEATURE:
<223> OTHER INFORMATION: Reverse primer for amplifying DNA encoding
      homeodomain of Msx1

<400> SEQUENCE: 4
attggatcct cactgcatct cttggddtt                                         29

US 8,012,925 B2

AGENT FOR INDUCING APOPTOSIS COMPRISING MSX1 OR A GENE ENCODING THE SAME AS AN ACTIVE INGREDIENT

CROSS-REFERENCE TO RELATED APPLICATION

This application claims priority to and the benefit of Korean Patent Application No. 10-2005-66541 filed in the Korean Industrial Property Office on Jul. 22, 2005, the contents of which are incorporated herein by reference.

FIELD OF THE INVENTION

The present invention relates to a novel use of Msx1 protein and nucleic acids encoding the same for modulating apoptosis. Particularly, the present invention relates to compositions for modulating apoptosis using Msx1 or nucleic acids encoding the same and use thereof in the treatment of disease states associated with abnormal apoptosis.

BACKGROUND OF THE INVENTION

Apoptosis, also called programmed cell death, is a form of cell death in which a series of programmed events leads to the destruction of cells (Kerr et al., British Journal of Cancer, 26: 239-257, 1972). Apoptosis plays an important role in an organism by controlling the normal development and providing a defense against many types of biological damages such as radiation, viral infections, and cancer through eliminating aged cells, unnecessary cells, and unhealthy cells, thereby leading to homeostasis of various tissues. The features of apoptosis vary among different cell types and depend upon the nature of the apoptotic stimulus, but some characteristics are common to all, that is, cell shrinkage, membrane blebbing, nuclear condensation, DNA fragmentation forming a "ladder" pattern upon electrophoresis (Kerr et al., British Journal of Cancer, 26: 239-257, 1972).

In particular, the ability to undergo apoptosis is closely associated with cancer development in that a reduction in such apoptotic ability would result in the retention of cells with unrepaired DNA damage and a consequent increased risk of mutations, which may lead to development of cancer.

The p53 gene is the most frequent target of genetic alteration in human cancers. p53 plays a critical role in maintaining cellular homeostasis and tumor-free survival of the organism by modulating cell cycle progression or apoptosis (Vogelstein et al., Nature 408:307-310, 2000; Vousden et al., Nat. Rev. Cancer 2:594-604, 2002). The p53 protein functions as a transcription factor with a high affinity for specific DNA target sequences in response to DNA damage or hypoxia. It selectively destroy stressed or abnormal cells to prevent the progression to cancer (Oda et al., Cell 102:849-862, 2000).

Therefore, inactivation of p53 is closely related with development of cancerous states, and such inactivation may or may not involve mutation(s) in the p53 gene. In the former case, p53 protein itself becomes non-functional due to a mutation in the p53 gene, while in the latter case, wild-type p53 protein is expressed, but the function thereof is inactivated by some other mechanism. For example, various p53 mutations including a point mutation are found in about 50% of cancer in human beings, but in many other cancer cells, p53 protein can be inactivated through an interaction with viral and cellular proteins. Therefore, in cells where the wild-type 53 protein is expressed but no longer functional, the reactivation of p53 to induce an apoptosis can provide an effective means to treat cancers.

The function of p53 protein is regulated by several mechanisms, including post transcriptional modification, stabilization, protein interactions, and subcellular localization. Among them, the regulation of p53 protein stability is one of the most effective mechanisms, and in fact several oncoproteins are shown to be involved in the generation of cancer by destabilizing the p53 protein.

The stability of p53, in normal cells as well as in malignant cells, is regulated by ubiquitin-dependent proteolysis, and Murine double minute 2 (Mdm2) oncoprotein is the most important regulator in this process and is involved in the nuclear export and degradation of p53. Thus uncontrolled regulation of Mdm2 may give rise to a cancer cell (Ashcroft et al., Oncogene 18:7637-7643, 1999; Yang et al., Oncogene 23: 2096-2106, 2004; Boyd et al., Nat. Cell Biol. 2: 563-568, 2000). The high risk human papillomavirus (HPV), which is implicated in the pathogenesis of cervical cancer, also produces E6 protein that is involved in the degradation of p53 in HPV-positive cervical cancer cells (Hausen et al., J. Natl. Cancer Inst. 92: 690-698, 2000, Hengstermann et al., Proc. Natl. Acad. Sci. U.S.A., 98: 1218-1223, 2001). A complete switch from Mdm2 to E6-dependent degradation of p53 has been shown to occur in HPV-positive cervical cancer cells. Consistent with this, the expression of peptides that specifically bind to E6 results in p53 accumulation and apoptosis in HPV-positive cancer cells (Butz et al., Proc. Natl. Acad. Sci. U.S.A., 97: 6693-6697, 2000). Therefore, for the treatment of cancer with wild-type p53 with impaired function, the reactivation of p53 to restore its apoptotic function may provide the most effective therapy.

Previously, there have been many efforts to discover proteins that interact with p53 and thereby regulate its activity. For example, US patent application publication No. 2004/0038243 discloses p53AIP1, a regulator of apoptosis by inhibiting p53, which was discovered through a screening of genes that are induced by p53.

International Patent Publication No. WO 2004/035580 discloses a low molecular weight chemical compound that was shown to be involved in recovering the apoptosis-inducing activity of p53.

US patent application publication No. 2004/253595 discloses p53-dependent Damage-Inducible Nuclear Protein 1 (p53DINP1) which regulates p53 by phosphorylating serine residue at position 63, thereby inducing p53-dependent apoptosis.

There remains, however, a significant need for a p53 regulator with improved efficacy in modulating p53 dependent apoptosis and having the ability to interact with inactivated p53 protein and to restore its apoptotic function, which none of the above publications disclose.

The information disclosed in this background of the Invention section is only for enhancement of understanding the background of the invention and therefore, unless explicitly described to the contrary, it should not be taken as an acknowledgement or any form of suggestion that this information forms the prior art that is already known in this country to a person of ordinary skill in the art.

SUMMARY OF THE INVENTION

The present invention has been made in an effort to provide therapy that is capable of effectively modulating apoptosis in tissues such as in tumors where the induction of apoptosis is desirable. The present inventors have discovered that Msx1 can effectively induce apoptosis in cells or tissues where the apoptosis is prevented from occurring due to an inactivation of p53 protein or absence of p53 protein.

The present invention therefore contemplates the induction of apoptosis in tissues by administering to a tissue or a subject associated with a disease condition a therapeutically effective amount of an Msx1 protein or a nucleotide sequence encoding the same.

The present invention further contemplates a method of modulating p53 protein activity in a tissue or a subject comprising a step of administering to a tissue or a subject associated with a disease condition a therapeutically effective amount of Msx1 protein or a nucleotide sequence encoding the same.

In one aspect, said Msx1 or a nucleotide sequence encoding the same is a homeodomain region of Msx1 or a nucleotide sequence encoding the same.

In another aspect, said modulation of apoptosis or p53 activity involves a direct interaction of Msx1 or homeodomain thereof with p53 protein.

In a further aspect, said interaction of Msx1 or homeodomain thereof with p53 protein leads to increased stability, and/or nuclear localization of p53, which is a clear implication for modulation of apoptosis by Msx1 via control of p53.

In a still further aspect, said p53 protein may be of endogenous or exogenous origin depending on the cell or tissues to be treated which may contain inactivated p53 protein or may not contain p53 at all.

The present invention also contemplates pharmaceutical compositions for inducing apoptosis in a target mammalian tissue, comprising Msx1 protein or a nucleotide sequence encoding the same as an active ingredient and a pharmaceutically acceptable carrier or excipient.

In a still further aspect, the cells or tissues to be treated with Msx1 protein or a nucleotide sequence encoding the same, or a pharmaceutical composition comprising Msx1 protein or a nucleotide sequence encoding the same of the present invention can be used for any cell or tissue where modulation and particularly induction of apoptosis are desirable. Exemplary cells or tissues include, but are not limited to, various tumors. Hence, the methods and compositions of the present invention are useful for treating disease conditions where apoptosis is inhibited. Such conditions include, for example, solid tumors, including but not limited to colon cancers, cervical cancers, ovarian cancers, lung cancers, lymphomas, breast cancers, prostate cancers, lymphomas, and renal cell cancers.

DETAILED DESCRIPTION OF THE PREFERRED EMBODIMENTS

Figure 1A:
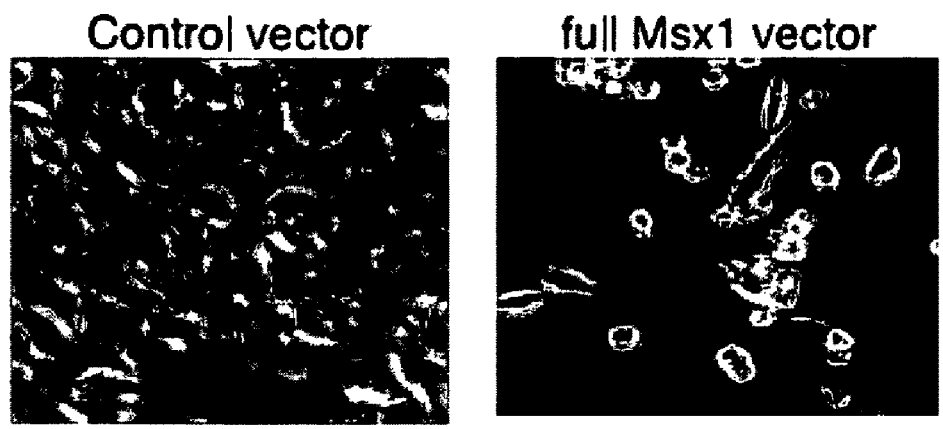
FIG. 1A shows microscopic images of cell morphology undergoing apoptosis (right) compared to control cells.

In order that the present invention herein described may be fully understood, the following detailed description is set forth.

Unless otherwise defined, all technical terms used herein have the same meaning as commonly understood by one of ordinary skill in the pertinent art. Commonly understood definitions of molecular biology terms can be found in, for example, Rieger et al., Glossary of Genetics: Classical and Molecular, 5th edition, Springer-Verlag: New York, 1991; and Lewin, Genes VIII, Oxford University Press: New York, 2004.

The present invention is based on the discovery of a novel use of Msx1 for modulating apoptosis through direct interaction with p53. It has also been discovered that Msx1 protein exerts its function through a homeodomain. The present invention therefore provides methods and compositions for modulating and particularly for inducing apoptosis in cells or tissues using Msx1 protein or the homeodomain thereof, or a nucleotide sequence encoding the same. In another aspect, the present invention provides methods and compositions for modulating p53 activity using Msx1 protein or the homeodomain thereof, or a nucleotide sequence encoding the same, In one embodiment, the expression of Msx1 resulted in the induction of apoptosis and inhibition of cell growth in HeLa cells (See FIGS. 1A to 1D).

In another embodiment, homeodomain spanning residues 166 to 225 of Msx1 were found to be sufficient to cause such apoptotic functions of Msx1 (See FIGS. 3A to D and 4A to 4E). In a further embodiment, the homeodomain of Msx1 showed a direct interaction with p53, indicating a novel function as a protein-protein interaction motif as opposed to a DNA binding motif as previously known (See FIG. 3B).

Msx1 is a 32 kDa protein containing a homeodomain, and it functions as a transcriptional repressor through its interactions with components of the core transcription complex as well as other homeoproteins. Msx1 is expressed at sites where cellular proliferation and apoptosis occur during a pattern of embryogenesis (Bendall et al., Gene 249:17-31, 2000), but its role in apoptosis as a regulator of p53 protein has not been known previously. The homeodomain is an evolutionarily conserved 60 amino acid DNA-binding domain. A homeobox gene containing the homeodomain functions as an essential transcriptional regulator in a variety of developmental processes (McGinnis et al., Cell 68: 283-302, 1992; Bendall et al., Gene 247: 17-31, 2000), however, its role as a regulator of p53 tumor suppressor in adult tissues is not known.

Msx1 or the homeodomain thereof for the methods and the compositions of the present invention encompass purified protein, biologically active protein fragments, recombinantly produced Msx1 or fragments thereof or fusion proteins, or gene/nucleic acid expression vectors for expressing Msx1 or any functionally equivalent variant thereof, all of which can be prepared by methods that are well-known in the art.

Further, Msx1 or the homeodomain thereof for the present invention or a gene encoding the same may be selected from known sequences of various origins including, but not limited to, human or mouse.

As used herein, the term "gene" is well-known in the art and refers to a nucleic acid sequence defining a single protein or polypeptide. It will be readily recognized by those of ordinary skill that the nucleic acid sequence of the present invention can be incorporated into any one of numerous kits which are well-known in the art.

As used herein, the term "functionally equivalent variant" refers to a protein or nucleic acid molecule which is substantially similar in biological activity to the protein or nucleic acid of wild-type Msx1 or the homeodomain thereof of the present invention. Such functionally equivalent variant encompasses any Msx1 protein or homeodomain thereof that is capable of interacting with p53 and includes, but is not limited to, those having base insertions, deletions, or substitutions that may be generated spontaneously or artificially by methods that are well-known in the art, e.g., by primer-directed PCR (Kramer, W. & Fritz, H J. Methods in Enzymology (1987) 154:350-367), "error-prone" PCR (Cadwell, R. C. and G. F. Joyce, PCR methods Appl (1992) 2:28-33), "gene-shuffling" called PCR-reassembly of overlapping DNA fragments, and the like.

Also encompassed by the present invention is a mutant at the nucleic acid level that does not change an amino acid such as a degenerate variant due to the degeneracy of the genetic code.

A nucleic acid sequence encoding Msx1 protein or the homeodomain thereof for the present invention encompasses genomic DNA, cDNA, and synthetic or recombinantly produced DNA, all of which can be prepared by methods that are well-known in the art. For example, genomic DNA is extracted from cells expressing Msx1 protein or the homeodomain thereof, which is subsequently used for the construction of a genomic library using vectors such as plasmid, phage, cosmid, BAC, and PAC followed by colony hybridization or plaque hybridization depending on the vectors to screen the Mxs1 genomic DNA using a probe with a sequence specific for the Msx1 gene or the homeodomain thereof of the present invention. For the preparation of cDNA, mRNA extracted from cells expressing Msx1 protein or the homeodomain thereof is used to synthesize first strand cDNA by reverse-transcription followed by PCR for the amplification of cDNA encoding Msx1 protein or the homeodomain thereof using primers specific for Msx1 or the homeodomain thereof of the present invention.

Preferably, such functionally equivalent variant or isolated sequence fragment is at least 50%, more preferably 70%, and most preferably 90% homologous to the corresponding part of the natural human Msx1 or the homeodomain thereof.

For example, for the purpose of the present invention, an Msx1 protein sequence with, but not limited to, NCBI (National Center for Biotechnology Information) accession no. AAH21285 (with or without signal sequences of amino acid residues 1-73 of SEQ ID NO:1) comprising amino acid residues 74-370 of SEQ ID NO:1 referred to herein as Msx1 (1-297), or a gene encoding the same with, but not limited to, GenBank accession no. BC021285 (represented by SEQ ID NO:2) may be used.

As mentioned hereinabove, Msx1 protein or the homeodomain thereof, or a nucleotide sequence encoding the same of the present invention can effectively induce apoptosis in a cell through direct interaction with p53 via homeodomain. Further, the present inventor has found that such interaction subsequently leads to increased stability, and/or nuclear localization of p53.

The function of p53 is regulated by several mechanisms including post translational modification, stabilization, protein interactions, and subcellular localization. One of the most effective mechanisms is regulation of p53 protein stability. The p53 protein has a very short half-life and therefore can be hard to detect in normal tissue. The stability is regulated by ubiquitin-dependent proteolysis, where Murine double minute 2 (Mdm2) is responsible for the unbiquitination of p53. Such ubiquitination, however, is prevented in the phosphorylated p53 (Honda et al., EMBO 18:22-27, 1999; Haupt et al., Nature 387:296-299, 1997). Therefore, the phosphorylation of p53 and its localization into a nucleus, and degradation of p53 are very closely related to each other.

In one embodiment of the present invention, the expression of Msx1 resulted in the nuclear localization of p53 protein corresponding to the increased stability of p53 protein. Specifically, the expression of Msx1 acted on the p53 at the protein level by increasing the half-life two-fold without affecting the mRNA level (FIG. 2B), thus increasing the level of p53 protein present in cells.

The above results clearly demonstrate that Msx1 protein of the present invention has a novel function of inducing nuclear localization of p53, thus increasing the stability of p53. Any functionally equivalent variant of wild-type p53 proteins that are able to interact with Msx1 of the present invention falls within the scope of the present invention.

In a further embodiment, p53 may be of endogenous or exogenous origins, or it may be a wild-type protein which is either functional or inactivated by some mechanism known to inactivate p53. For example, such mechanisms involve an interaction of p53 with a viral protein including, but not limited to, SV40 large T-antigen, E1B protein of adenovirus, E6 of papilloma virus, and EBNA-5 of Epstein bar virus. In one embodiment, not only the cells having endogenous p53 protein, but also the cells deficient of p53 protein, into which exogenous p53 was introduced prior to or during the treatment with Msx1, equally responded to the treatment with Msx1.

The Msx1 or homeodomain thereof, or a nucleotide sequence encoding the same, and a pharmaceutical composition containing the same can therefore be used effectively to treat cells or tissues associated with the disease condition where the induction of apoptosis is desirable regardless of the presence of endogenous p53 protein. In one embodiment, such disease conditions are related with an inactivation or absence of p53, and are preferably mediated or resulting from the inactivation or absence of p53. In another embodiment, a disease condition where p53 proteins are absent or inactivated includes, but is not limited to, tumors such as colon cancers, cervical cancers, ovarian cancers, lung cancers, lymphomas, breast cancers, prostate cancers, lymphomas, and renal cell cancers.

Specifically, for solid tumors characterized by an uncontrolled tumor progression and metastasis, where eradication of cancer cells by apoptosis is desirable, Msx1 or the homeodomain thereof, or a nucleotide sequence encoding the same of the present can be effectively used. In one embodiment, the ectopic expression of Msx1 of the present invention was able to effectively suppress the growth and progression of cervical cancer cells (See FIGS. 5A to 5C). This inhibition of tumor growth was confirmed to result from apoptosis as indicated by the dramatic increase of proteins involved in apoptosis.

For the expression of Msx1 or the homeodomain thereof for the methods and compositions of the present invention, Msx1 or the homeodomain gene or functional variant thereof as described herein is operatively linked into a vector. The choice of said vector depends, as is well-known in the art, on the desired level of protein expression, the host cell to be transfected, and the like. A vector contemplated by the present invention is at least capable of directing the replication and expression of a gene included in the vector in cells, preferably in eukaryotic cells.

Such eukaryotic expression vectors encompass both viral and non-viral vectors, and are familiar to one of ordinary skill in the pertinent art. For non-viral vector systems, see examples of Ausebel, et al., in Current Protocols in Molecular Biology, Wiley and Sons, New York (1993) and of Sambrook et al, Molecular Cloning: A Laboratory Manual, Cold Spring Harbor Laboratory (1989). In addition, they are commercially available from several sources. Typical of such vectors are pcDNA 3 or 4, pRc/CMV (Invitrogen, Carlsbad, Calif., USA), pSVL, and pKSV-10 (Amersham Pharmacia Biotech, Piscataway, N.J., USA).

The viral expression vectors for the expression of Msx1 or the homeodomain thereof include infectious vectors such as recombinant DNA viruses and adenoviral or retroviral vectors which are engineered to express the desired protein and have features that allow infection of target tissues, for example, such viral vectors are used encapsulated by a viral coat, which is familiar to one of ordinary skill in the pertinent art (see Logan et al., Proc. Natl. Acad. Sci., USA (1984) 81:3655-3659; Mackett et al., Proc. Natl. Acad. Sci., USA (1982) 79:4927-4931; Cone et al., Proc. Natl. Acad. Sci., USA (1984) 81:6349-6353). Further, retroviral/adenoviral expression systems can be readily adapted for practice of the methods and compositions of the present invention. For example, see Karavanas et al., Crit. Rev. in Oncology/Hematology (1998) 28:7-30 for retroviral viral vectors, and Gene Expression Systems ed., Fernandez and Hoeffler, Academic Press, San Diego, USA, 1990, for adenoviral expression systems. In one embodiment, Msx1 is expressed using adenoviral expression systems such as described in Park et al., Cancer Res 65:749-757, 2005.

In one aspect, the present invention provides a method for inducing apoptosis in a tissue and a subject with a disease condition, where such disease condition is preferably mediated or resulting from the inactivation or absence of p53. In a further aspect, the present invention also provides modulating p53 in a tissue and a subject with a disease condition, where such disease condition is preferably mediated or resulting from the inactivation or absence of p53. The method comprises administering to said tissue or subject a therapeutically effective amount of Msx1 or the homeodomain thereof or a nucleotide sequence encoding the same.

As used herein, the term "therapeutically effective" amount refers to an amount of Msx1 or a nucleotide sequence encoding the same that is sufficient to produce a measurable modulation, preferably induction, of apoptosis in tissue or a subject. Modulation of apoptosis is measured by methods known to one skilled in the art, for example, those described in the Examples.

The tissue to be treated may be any of a variety of tissues, or organs including cervix, ovary, skin, muscle, gut, connective tissue, brain tissue, bones, and the like in which a tumor can arise mainly due to a inactivation of p53 or the absence of p53.

The subject is a patient to be treated, wherein the patient is a human as well as a veterinary patient.

The pharmaceutical composition containing Msx1 or the homeodomain thereof or a nucleotide sequence encoding the same of the present invention is administered in a manner compatible with the dosage formulation, and in a therapeutically effective amount, for example intravenously, intraperitoneally, intramuscularly, subcutaneously, and intradermally. It may also be administered by any of the other numerous techniques known to those of skill in the art, see for example the latest edition of Remington's Pharmaceutical Science, the entire teachings of which are incorporated herein by reference.

For example, for injections, Msx1 or the homeodomain thereof, or a nucleotide sequence encoding the same of the present invention may be formulated in adequate solutions including but not limited to physiologically compatible buffers such as Hank's solution, Ringer's solution, or a physiological saline buffer. The solutions may contain formulatory agents such as suspending, stabilizing, and/or dispersing agents. Alternatively, Msx1 or the homeodomain thereof or a nucleotide sequence encoding the same of the present invention may be in powder form for combination with a suitable vehicle, e.g., sterile pyrogen-free water, before use.

Further, the composition of the present invention may be administered per se or may be applied as an appropriate formulation together with pharmaceutically acceptable carriers, diluents, or excipients that are well-known in the art.

In addition, other pharmaceutical delivery systems such as liposomes and emulsions that are well-known in the art, and a sustained-release system, such as semi-permeable matrices of solid polymers containing the therapeutic agent, may be employed. Various sustained-release materials have been established and are well-known to one skilled in the art.

Further, the composition of the present invention can be administered alone or together with another therapy conventionally used for the treatment of angiogenesis, tumor progression, and/or metastasis related diseases, such as surgical operation, hormone therapy, chemotherapy, or biological agents.

The quantity to be administered and timing may vary within a range depending on the formulation, the route of administration, and the tissue or subject to be treated, e.g., the patient's age, body weight, overall health, and other factors. For the nucleic acid sequence, the amount administered depends on the properties of the expression vector, the tissue to be treated, and the like. The suitable amount can be measured by the amount of vector used, or the amount of expressed protein expected. The exact formulation, route of administration, and dose can be chosen by the individual physician in view of the patient's condition (see, for dose and dosing schedule, e.g., latest editions of Remington's Pharmaceutical Science, Mark Publishing Co., Easton, Pa.; and Goodman and Gilman's: The Pharmacological Basis of Therapeutics, Pergamon Press).

The dosage of Msx1 or the homeodomain thereof or a nucleotide sequence encoding the same of the present invention preferably falls within a range of concentrations that include the effective dose with little or no toxicity, but that are sufficient to produce a measurable modulation, preferably inhibition, of angiogenesis, tumor progression, and metastasis in tissue or a subject. A single dose of Msx1 or the homeodomain thereof or a nucleotide sequence encoding the same administered will typically be in the range of about 0.05 to about 10 mg/kg of patient weight. The Msx1 or the homeodomain thereof or a nucleotide sequence encoding the same of the present invention will typically be formulated in a suitable formulation at concentrations of about 0.001 mg/ml to 100 mg/ml such that the final dose is about 0.05 to 10 mg/kg of patient body weight. For viral vectors, the recombinant virus containing such viral vectors will typically be in the range of about $10^3$~$10^{12}$ pfu/kg per kg of body weight.

The following examples illustrate the present invention in further detail. However, it is understood that the present invention is not limited by these examples.

Example 1

Construction of Various Expression Vectors

Figure 3A:
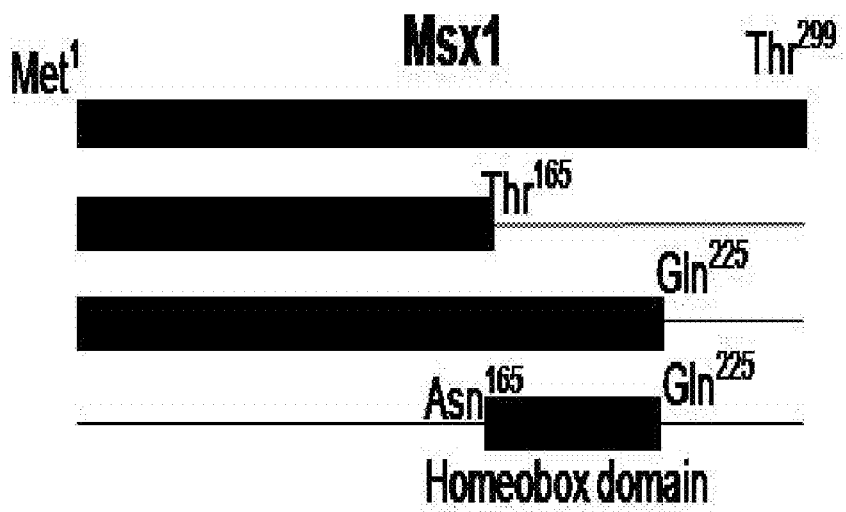
FIG. 3A is a schematic representation of Msx1 and p53 proteins showing various deletions and domains that are important for cellular activity.
Figure 3A:
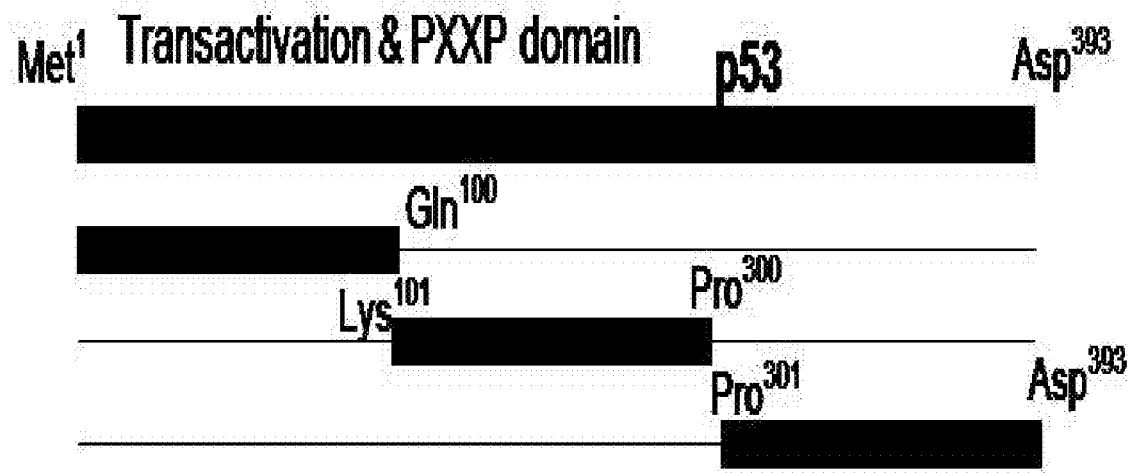

Various viral and non-viral vectors containing Msx1 or various deletion products thereof as in FIG. 3A, or containing p53, were constructed and used to investigate the activity of Msx1 of the present invention as previously described (Park et al., Cancer Res. 65: 749-757, 2005; Hwang et al., Int. J. Gynecol. Cancer 8: 27-36, 1998).

Adenoviral Vectors

Briefly, for viral constructs, adenoviral expression systems were used. An adenoviral vector pΔACMVMsx1(Ad-Msx1) encoding Msx1 was prepared by subcloning 0.9 kb of an Msx1 fragment of human origin into a BamHI site in multi-cloning sites of pΔACMVp(A). An adenoviral vector Ad-p53 encoding p53 was prepared as previously described (Hwang et al., Int. J. Gynecol. Cancer 8: 27-36, 1998). For the production of replication deficient adenoviruses, adenoviral constructs as described above and pJM17 carrying adenoviral genomic DNA (F. Graham, McMaster University, Ontario, Canada) were cotransfected to HEK 293 cells and purified by CsCl gradient centrifugation followed by extensive dialysis against PBS (Phosphate Buffered Saline) supplemented with 10% glycerol and μmol/L $MgCl_2$. The titer of each adenovirus produced was determined by plaque assay using HEK 293 cells and expressed as pfu (Plaque Forming Unit).

Plasmid Vectors

Plasmid vectors, pCB6/Msx1 encoding full length human Msx1, and pGEX-2T-Msx1 (1-297) and pGEX2T-Msx1 (1-165) expressing Msx1 protein (amino acid residues 1-297 and 1-165, respectively) fused to Glutathione S Transferase (GST) were previously described (Zhang et al., Mol. Cell. Biol. 17: 2920-2932, 1997). The residue numbers provided are from human Msx1 protein sequence of NCBI accession no. AAH21285, and signal peptides (original amino acid residues 1 to 73) are not counted.

Plasmid vectors expressing full length (pEGFP/Msx1(1-297)) or various deletion products (pEGFP/Msx1(1-165), pEGFP/Msx1(1-225), pEGFP/Msx1(166-225)) of Msx1 fused to Enhanced Green Fluroescent Protein (EGFP) were previously described (Park et al., ibid). The numbers in each of the plasmids above indicate amino acid residues of Msx1 protein contained in each corresponding vector. Briefly, BamHI-HindIII fragments of pGEX2T-Msx1(1-297) and BamHI-EcoRI fragments of pGEX2T-Msx1(1-165) were subcloned into BglII-HIndIII and BglII-EcoRI sites of pEG-FPC1 (Clontech, Mountain View, Calif., USA), respectively. The DNA encoding homeodomain of Msx1 (referred to herein as amino acid residues 166-225 of Msx1 which corresponds to amino acid residues 239-298 of SEQ ID NO:1) was amplified by PCR using pEGFP (1-297) as a template and 5'attgtctacaaccggcaagcccaggacgcct-3' (SEQ ID NO:3) and 5' attggatcctcactgcatctcttggddtt-3' (SEQ ID NO:4) as forward and reverse primers, respectively. Subsequently, the amplified DNA product was subcloned into SAlI and BamHI sites of pEGFP to create pEGFP (166-225).

The correctness of the cloned sequence of each plasmid constructed and used for the present invention was confirmed by DNA sequencing of the constructs.

pGST-p53 and pCMV-p53 plasmid vectors were previously described (Park et al., Journal of Virology 74(24): 11977-11982, 2000).

Example 2

Cell Culture and Transfection

Cervical cancer cell line HeLa ((American Type Culture Collection, USA), Human lung cancer cell line H1299 (American Type Culture Collection, USA), and HEK 293 (Clonetics, San Diego, Calif., USA) were cultured as described (Lee et al., Oncogene (2001) 20:6700-6776; Park et al. ibid). Briefly, the HeLa, H1299, and HEK 293 cells were cultured in DMEM (Dulbecco's Modification of Eagles Medium) and EMEM (Eagles Minimum Essential Medium), respectively, each supplemented with 10% FBS and antibiotics (Life Technologies, Gaithersburg, Md., USA). The cells were incubated at 37□ in a 5% $CO_2$/95% air atmosphere.

DNA transfection into each of the above cell lines and adenoviral infection were carried out as described (Lee et al., Oncogene (2001) 20:6700-6776; Park et al., ibid);

Example 3

The Apoptosis Inducing Activity of Msx1

The activity of Msx1 for inducing apoptosis was investigated as described (Park et al., ibid). Briefly, HeLa cells were seeded onto each well of 4-chamber slides (Nalgene Nunc, Rochester N.Y., USA) at $5 \times 10^4$ cells/well and then transfected with pEGFP/full length Msx1 and empty pEGFP vectors as prepared in Example 1 for 24 hours using Effectene™ (Qiagen, Hilden, Germany) as recommended by the manufacturer.

The transfected HeLa cells were then tested for apoptosis by morphologic alterations of whole cells using a light microscope (Zeiss, Hallbergmoos, Germany) as well as the nucleus, and by cell growth inhibition using an MTT calorimetric assay and FACS analysis as described (Park et al., ibid).

Figure 1B:
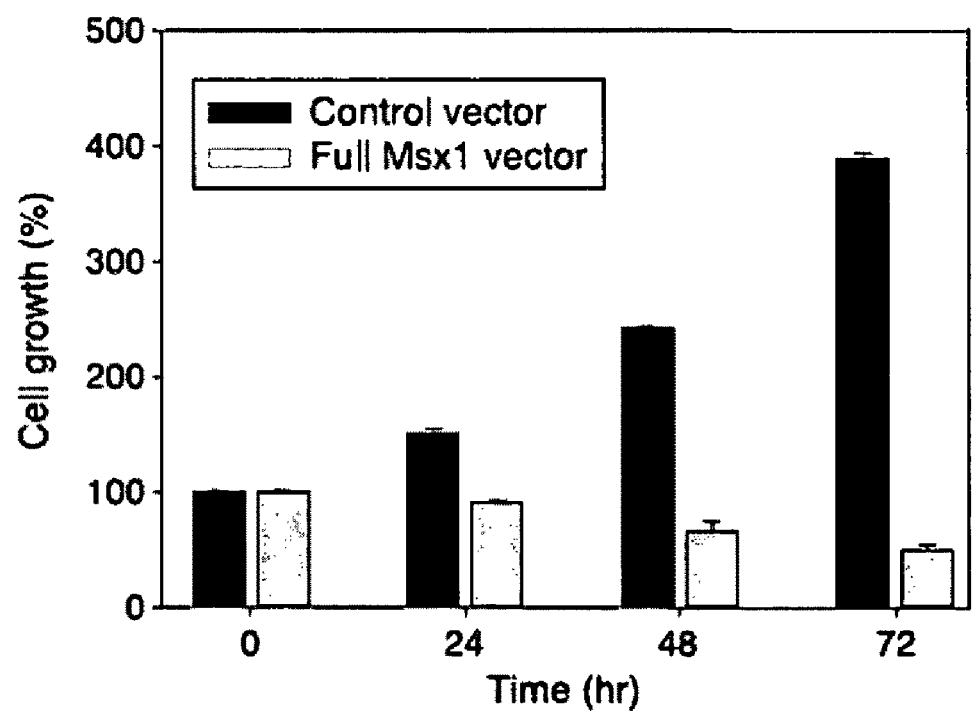
FIG. 1B shows a bar graph of the Msx1 mediated growth inhibition of cells determined by MTT calorimetric assay.

FIGS. 1A to 1D illustrate the Msx1-mediated induction of apoptosis in HeLa cells after the expression of a full length Msx1 gene (full Msx1 vector). As a control, cells containing only the vector without the Msx1 gene were used (control vector). As shown in FIGS. 1A to 1D, Msx1 caused a change in cell morphology (FIG. 1A) and a dramatic reduction in cell growth (FIG. 1B).

Further, to confirm that the reduction in cell number represents apoptosis, a change in nuclear morphology and FACS analysis were carried out as described (Part et al., ibid). Briefly, for evaluation of change in nuclear morphology, the transfected cells were fixed in methanol and stained with nuclear-specific dye, 4',6-diamidino-2-phenylindole (DAPI) (Sigma, USA), washed with 1×PBS thrice, followed by treatment with VectaShield® (Vector Laboratories, Burlingame, Calif., USA) and examination under a fluorescence microscope (Zeiss). For evaluation of change in cell growth, the transfected cells were incubated with FITC-labeled Annexin V and propidium iodide for 15 minutes according to the manufacture's protocol (Borehringer Mannheim, Mannheim, Germany) and then analyzed on a FACS (Fluorescence Activated Cell Sorter) Vantage (Becton Dickinson, San Jose, Calif.).

Figure 1C:
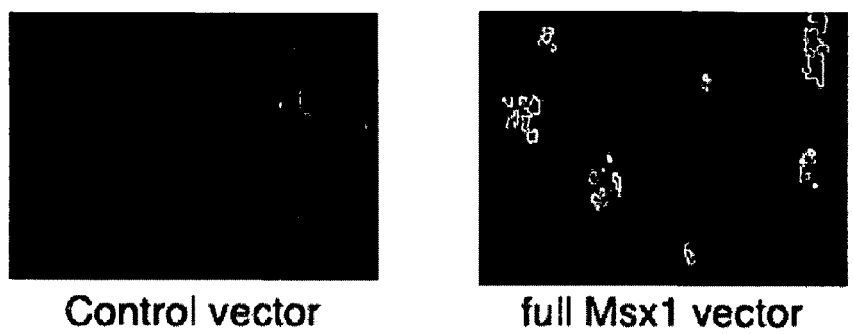
FIG. 1C shows fluorescent microscopic images of the nuclear fragmentation in full-length Msx1 expressing cells (right) whereas control cells have normal oval nuclei after staining with DAPI.
Figure 1D:
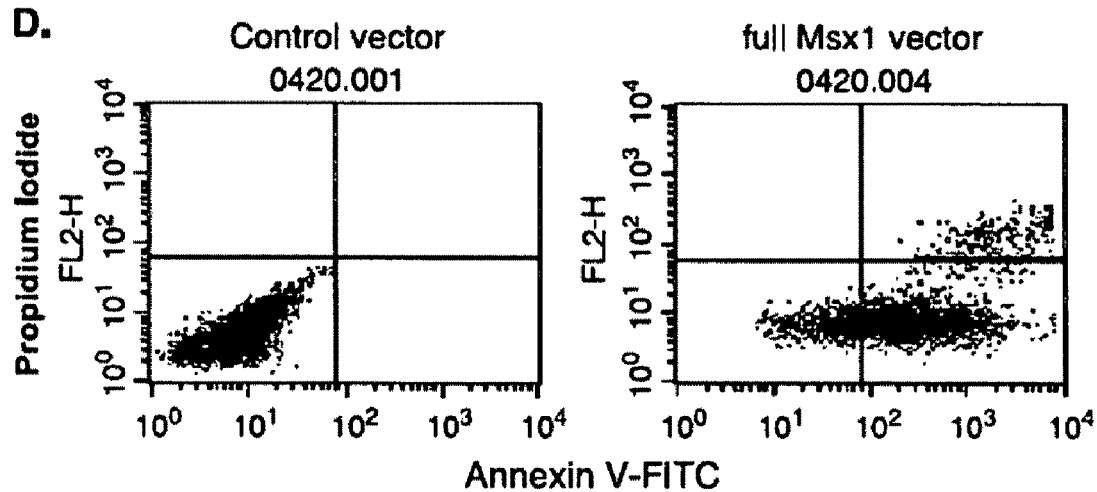
FIG. 1D shows FACS data of cells undergoing apoptosis after double stained with FITC-labeled Annexin V and propidium iodide.

As shown in FIGS. 1C and 1D, the cells expressing full length Msx1 showed fragmented nuclei which is characteristic of apoptosis, whereas control cells had normal oval shaped nuclei (FIG. 1C). Further, FACS analysis also demonstrated that the cells expressing full length Msx1 underwent apoptosis, as is evident by a low forward scatter (FCS) and a high side scatter (SSC) profile (FIG. 1D).

These results clearly indicate that Msx1 has a novel function of inducing apoptosis.

Example 4

Msx1 Causes Nuclear Localization, and Increased Stability of p53

4-1 Increased level of p53 by Msx1

To investigate the mechanism underlying Msx1 induced apoptosis, the levels of p53 mRNA and protein in HeLa cells were examined as previously described (Park et al., ibid). Briefly, total cellular RNA was isolated from HeLa cells transfected as in Example 3 using TRIzol Reagent (Life Technologies, Gaithersburg, Md., USA) as recommended by the manufacturer. For Northern blot analysis, 15 µg of total RNA per lane was separated by electrophoresis in a 1.2% agaroseformaldehyde gel, and the gel was blotted onto a nylon membrane. Each probe for specific detection for p53 and Msx1 was labeled with 32P using a Rapid hybridization kit (Amersham Pharmacia Biotech, Piscataway, N.J., USA)) and hybridized to the blot. For a detection of protein levels, a whole cell protein extract was prepared from HeLa cells transfected as in Example 3 using a lysis buffer (50 mmol/L, Tris-HCl (pH8.0), 150 mmol/L NaCl, 1% NP40, 0.1% SDS, and 10 mmol/L sodium deoxylate). For Western blot analysis, 15 µg of the whole cell extract per lane was separated by electrophoresis in a 10% SDS-polyacrylamide gel and the gel was blotted onto a nylon membrane. The blot was then incubated with an anti-Msx1 antibody or an ant-p53 antibody (Santa Cruz Biotechnology, Santa Cruz, Calif., USA), and bound antibodies were visualized with an ECL Chemiluminescent Kit (Amersham) as recommended by the manufacturer.

Figure 2A:
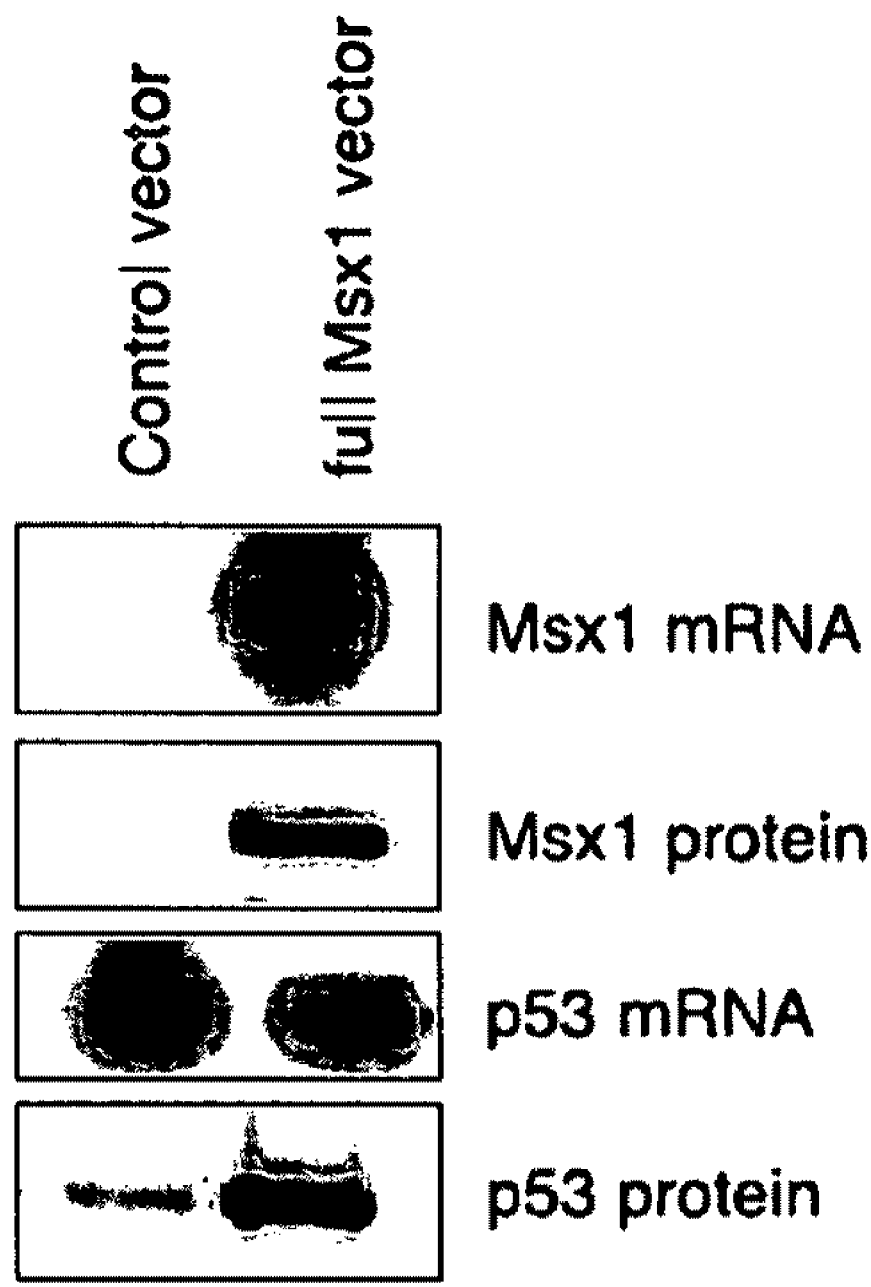
FIG. 2A shows the results of Northern blot (for the detection of mRNA level) and Western blot (for the detection of protein level) analysis showing that the expression of Mxs1 causes only the induction of p53 protein without inducing mRNA expression.
Figure 2B:
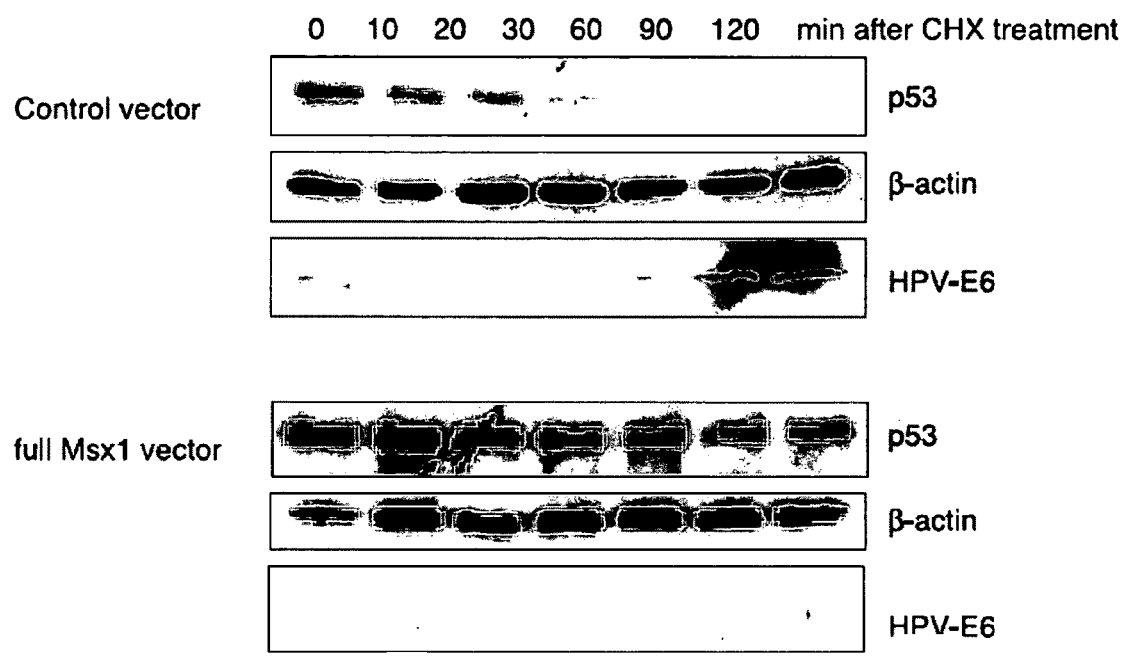
FIG. 2B shows the result of Western blot analysis showing that Msx1 increases the stability of p53 and HPV-E6 protein, wherein the beta-actin serves as a control for equal protein loading and control for normal protein expression.
Figure 2C:
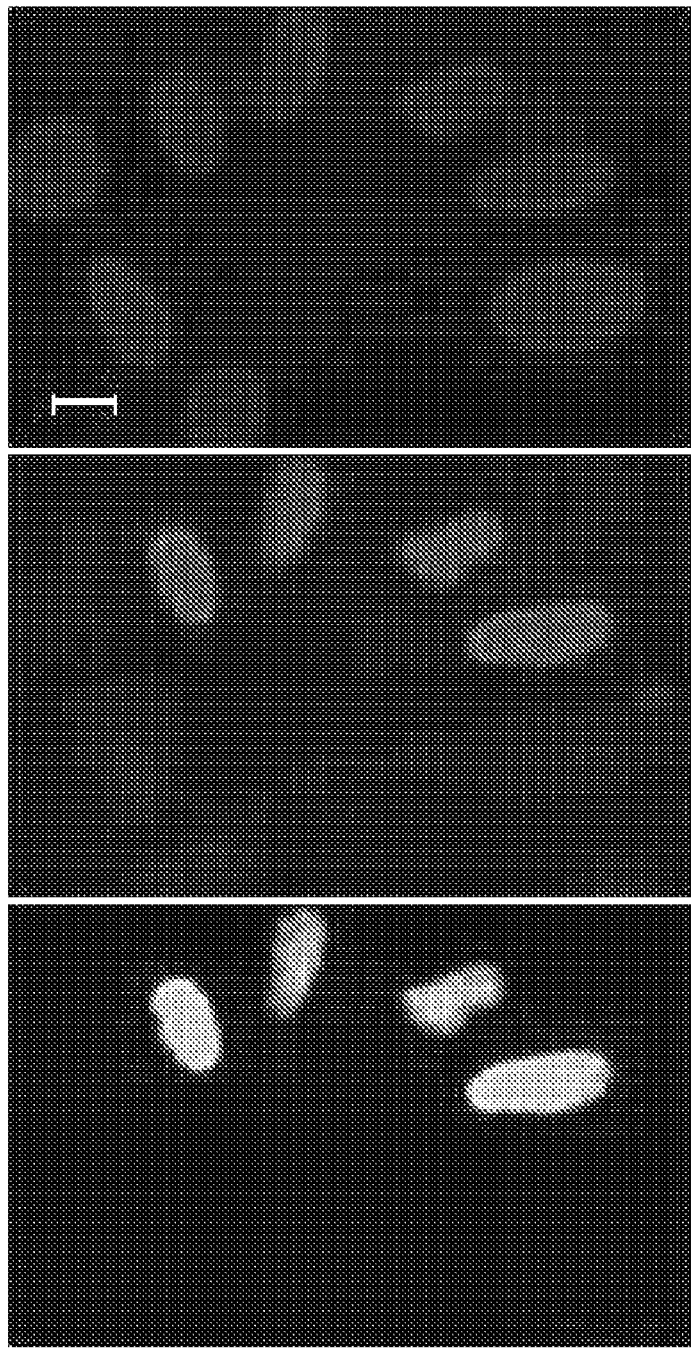
FIG. 2C shows fluorescent microscopic images of the nuclei and nuclear localization of p53 by Msx1 in the presence of E6, wherein the nuclei were stained with DAPI, Msx1 was detected by intrinsic fluorescence (green), and p53 protein (red) was detected by indirect immunofluorescence.

FIGS. 2A to 2C illustrate the effect of Msx1 on the kinetics of p53 stability determined using HeLa cells expressing a full length Msx1 (Full Msx1 vector). As a control, cells containing only the vector without the Msx1 gene were used (Control vector). As shown in FIG. 2A, Msx1 did not change the level of endogenous p53 mRNA, but it did increase the steady state level of endogenous p53 protein. These results indicate that Msx1 regulates p53 at the protein level.

4-2 Stabilization of p53 by Msx1

Because the intracellular level of p53 is primarily regulated by modulation of its stability, the kinetics of p53 degradation in cells expressing full length Msx1 was examined.

HeLa cells were transfected with a control vector or a full length Msx1-containing vector as in Example 3. At 24 hours post-transfection, cells were treated with cycloheximide for 10, 20, 30, 60, 90, and 120 minutes. Western blot analysis was then carried out as described above using anti-p53 (SantaCruz) or anti-HPV E6 (Ab-1) (Oncogene, Uniondale, N.Y., USA). Equal protein loading was confirmed by sequential incubation of the blot with anti-beta-actin antibody (SantaCruz). The intensity of the p53 bands was determined by densitometric analysis.

As shown in FIG. 2B, the half-life of p53 protein in control vector-transfected cells was less than 30 minutes, whereas the half-life of cells expressing Msx1 was 2 fold higher (60 minutes). This result is in agreement with that of FIG. 2A, and it indicates that the increase in the level of p53 as shown in FIG. 2A resulted from the increased half-life. The results could be a consequence of its decreased polyubiquitination mediated by HPV-encoded E6 protein that recruits the cellular ubiquitin-protein ligase E6-AP. The effect of Msx1 on E6 level was examined. FIG. 2B shows that the cellular level of E6 protein was detectable after 30 minutes in the control vector-transfected HeLa cells, and the E6 level remained undetectable in Msx1 expressing cells until 120 minutes after cycloheximide treatment. The stabilization of p53 coincides with the decrease in the cellular level of E6 protein.

These results strongly suggest that stabilization of p53 protein by Msx1 may result from a delay of E6 mediated p53 degradation.

4-3 Increased Nuclear Localization of p53 by Msx1

Since p53 subcellular localization is important for its function, indirect immunofluorescence was carried out to determine the subcellular localization of p53 in the presence of Msx1 as described (Park et al., ibid). Briefly, HeLa cells were transfected as described in Example 3, washed with 1×PBS, and fixed in 4% paraformaldehyde. The cells were then permeablized with 0.2% triton X-100, and blocked with 1% bovine serum albumin, and were then incubated with an anti-p53 antibody and subsequently with rhodamine-conjugated goat anti-mouse IgG (Jackson Immunoresearch Laboratory, Inc., West Grove, Pa., USA). Expression and localization of the proteins were observed under a confocal microscope (Bio-Rad, Hertfordshire, UK).

As shown in FIG. 2C, cells transfected with Msx1 had a clear nuclear accumulation of p53 (rhodamine: red), in contrast with the absence of p53 in the nuclei of cells transfected with a control vector without Msx1 (DAPI: blue).

These results clearly demonstrate that Msx1 has a novel function in p53 stabilization and subcellular localization.

Example 6

Interaction Between Msx1 and p53

6-1 Yeast Two Hybrid Analysis

To determine whether protein-protein interactions are involved, and which part of Msx1 are involved if any, in the stabilization of p53 leading to apoptosis of cells by Msx1, yeast two hybrid assays were used as previously described (Gyuris et al., Cell 75: 791-803, 1993; Part et al., ibid).

Briefly, to this end, four Msx1 constructs (FIG. 3A top) were made as described in Example 1. DNA fragments encoding full length human HPV-E6 and p53 proteins were isolated by PCR from the cDNA library derived from HeLa cells (Clontech) and cloned into pJG4-5 at unique EcoRI and XhoI sites for in-frame fusion of each cDNA with B42D activation domain. The truncated constructs of Msx1 as shown in FIG. 3A were obtained by PCR using specific set of primers designed for each deletion product and pCB6+/Msx1 as a template. Each amplified Msx1 fragment was then inserted into a pGlida vector (Clontech) using BamHI and XhoI sites to express it as a fusion protein with LexA. Each pGlida and pJG4-5 fusion construct prepared was then introduced into the testing yeast strain EGY48. The positive interactions between the fused proteins were revealed by cell growth for 3 days at 30° C. on a leucine-depleted medium containing 2% galactose, as well as by the formation of blue colonies on a synthetic medium containing 5-bromo-4-chloro-3-indolyl-β-D-galactoside (X-gal, 5 mmole/L)-X-gal, 2% galactose, and 2% raffinose. The binding activity between HPV-E6 and Msx1 was also determined quantitatively by the relative expression level of β-galactosidase as described (Rho, S B et al., FEBS Lett 557: 57-63, 2004; Rho, S B et al., PNAS USA 93:10128-33,1996).

Figure 3B:
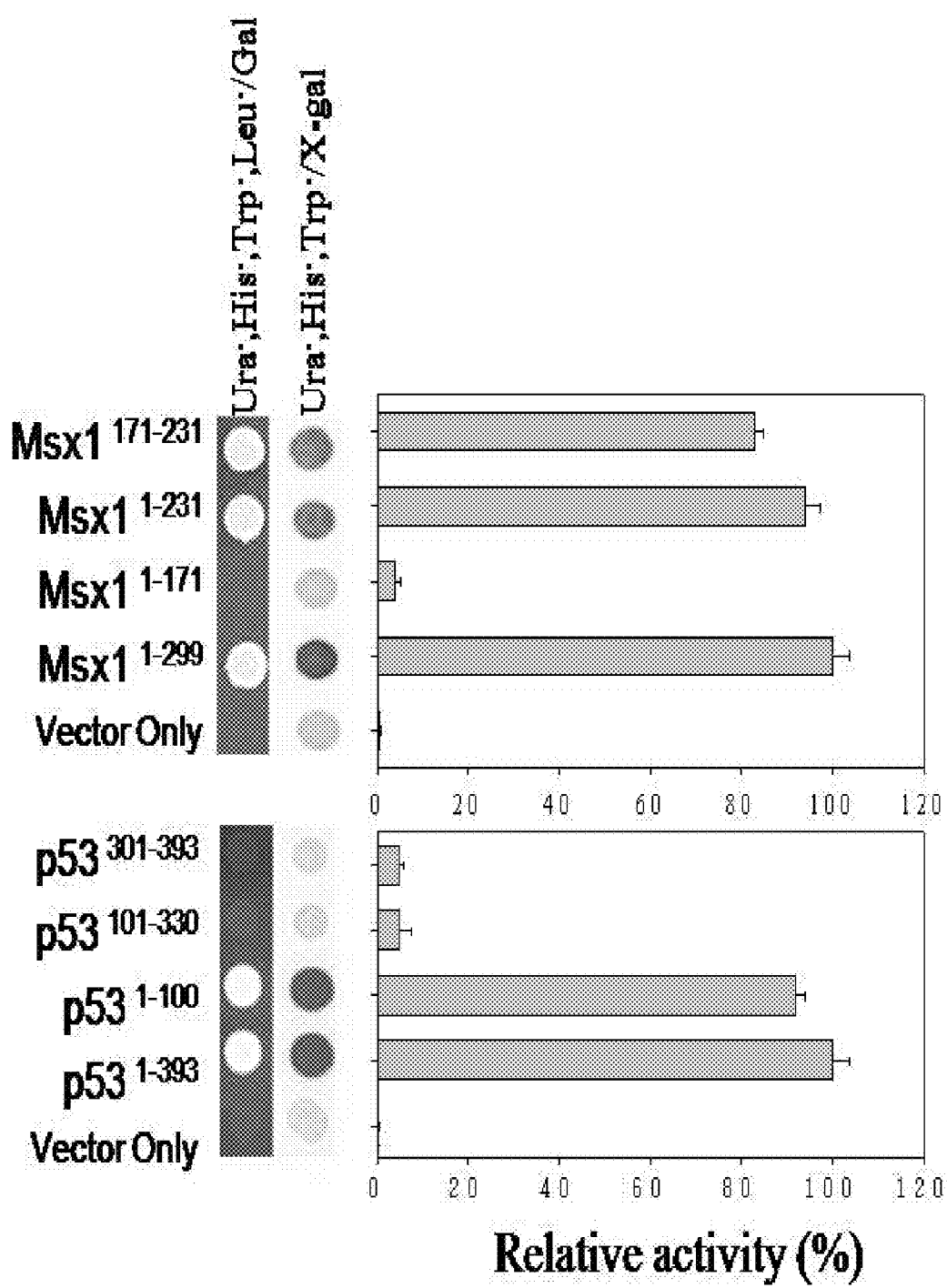
FIG. 3B shows the results of beta galactosidase lift assays of Yeast Two Hybrid analysis and a corresponding bar graph showing the binding activity between Msx1 and p53, wherein the interactions were presented by the relative activity of β-galactosidase.

FIGS. 3A to 3D illustrate the direct interaction of Msx1 with p53 protein. As shown in FIG. 3B (top), full-length Msx1 (1-297) and a truncated form of Msx1 containing homeodomain (1-225) as well as Msx1 homeodomain alone (166-225) interacted with p53 as indicated by the blue color of the colony harboring both of them. However, a construct lacking homeodomain (1-165) lost its interaction with p53 indicated by the while colony. These results demonstrate that the homeodomain alone was essential and sufficient for interaction with p53.

These results also demonstrate a novel function for the Msx1 homeodomain as a protein-protein interacting motif rather than as a DNA-binding motif as previously known.

The region of p53 that interacts with Msx1 was also determined as above. As shown in FIG. 3B (bottom), the $NH_2$ terminus of p53 encompassing both the transactivation domain and the PXXP domain was found to be involved in the interaction with the homeodomain of Msx1.

6-2 GST Pull Down Assay

To examine the interaction between p53 and Msx1 in human cells, a GST pull down assay in HeLa cells was carried out as described (Park et al., ibid).

Briefly, HeLa cells were cotransfected as in Example 3 with GST, GST-p53, and pCB6/Msx1 expression vectors constructed as described in Example 1, and then the whole cell lysates were prepared for a GST pull down assay. After pull down with glutathione agarose beads, immunoblot analysis was done using anti-p53(DO-1) and Msx1 antibodies as in Example 3.

Figure 3C:
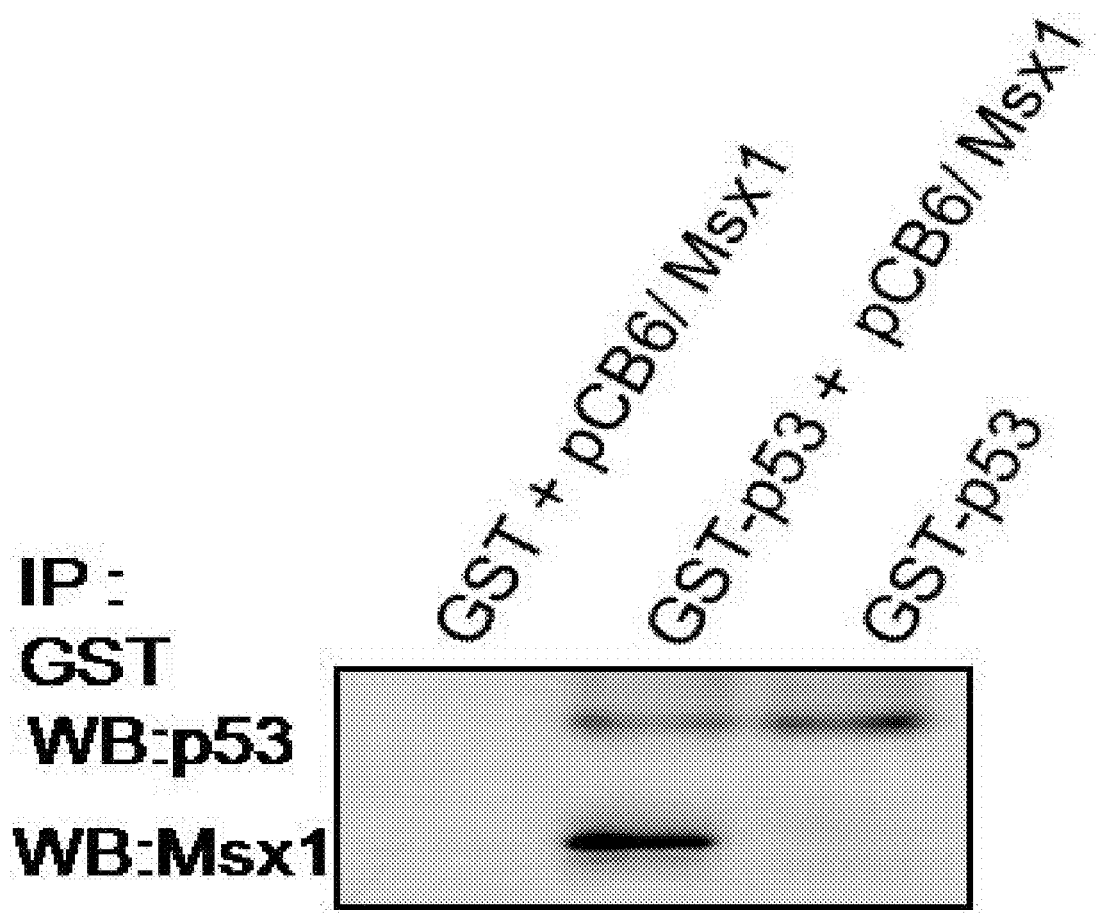
FIG. 3C shows the results of Western blot analysis after a GST pull-down assay with cell lysates expressing p53 fused with GST (GST-p53) and/or Msx1 (pCB6/Msx1), wherein the bound Msx1 and p53 were detected with anti-p53 and anti-Msx1 antibodies, respectively.

As shown in FIG. 3C, GST-p53 fusion protein efficiently pulled down Msx1, demonstrating a direct interaction between Msx1 and p53 in HeLa cells.

Figure 3D:
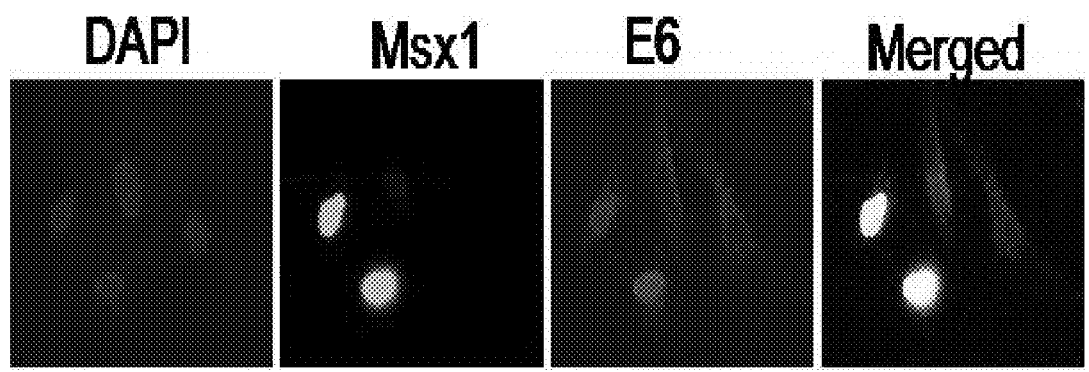
FIG. 3D shows florescent microscopic images showing a colocalization of Msx1 and E6 in the nucleus.

Further, indirect immunofluorescence carried out as in Example 5 showed strong accumulation of E6 and Msx1 in the nucleus of Msx1-expressing cells, whereas E6 was present in the cytoplasm of E6 of control cells (FIG. 3D).

Example 7

Homeodomain of Msx1 is Necessary for Induction of Apoptosis and p53 Stabilization Whether the homeodomain of Msx1 is important and sufficient for the stabilization of p53 and its apoptosis inducing function is determined based on the results of Example 6.

7-1 Induction of Apoptosis and Cell Growth Inhibition by the Homeodomain of Msx1

An Msx1 expression vector containing full length Msx1 (pEGFP/full Msx1) or Msx1 lacking a homeodomain (pEGPF/Msx1(-HD)) tagged with an enhanced EGFP coding sequence prepared as described in Example 1 was transiently expressed in HeLa cells, and the cells were examined for induction of apoptosis and colony formation by Western blot analysis as described (Park et al., ibid).

Briefly, induction of apoptosis was determined by the nuclear morphology which was observed by fluorescence microscopy after staining the cell with DAPI as in Example 3.

Figure 4A:
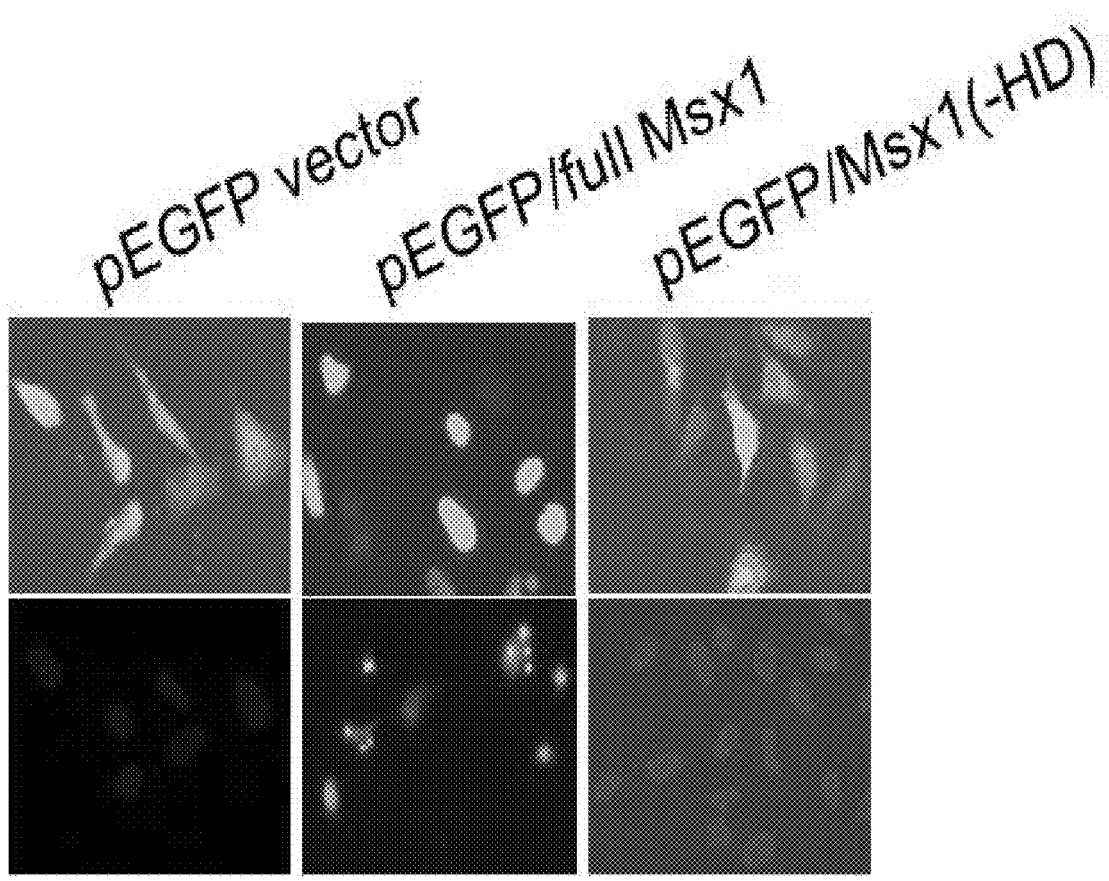
FIG. 4A shows microscope images showing the expression of Msx1 (top) and morphology of nuclei stained with DAPI (bottom).

FIGS. 4A to 4E illustrate that the homeodomain of Msx1 protein is important for the induction of apoptosis. A vector construct expressing Msx1 protein with a deletion of homeodomain (pEGFP/Msx1(-HD)) was used. As negative and positive controls, a vector without Msx1 (pEGFP) and with a full length Msx1 (pEGFP/full Msx1) gene were used, respectively. As shown in FIG. 4A, EGFP are expressed equally well in all cells (upper panel, EGFP; green color), and full-length Msx1 induced apoptosis in HeLa cells as evident by the presence of fragmented nuclei stained with DAPI (lower panel, DAPI: blue color). In contrast, HeLa cells transfected with either Msx1 lacking the homeodomain or with a control GFP vector did not induce apoptosis as evident by the presence of intact oval nuclei (lower panel).

Figure 4B:
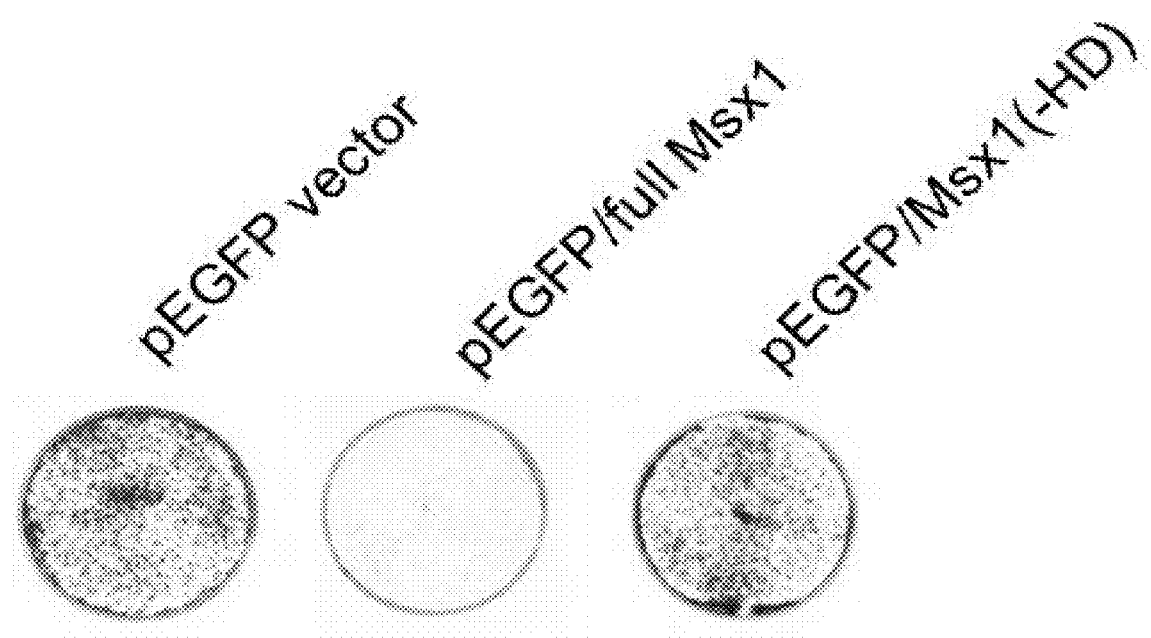
FIG. 4B shows the results of a colony formation assay stained with crystal violet showing that the deletion of homeodomain abrogates the apoptotic activity of Msx1 protein.

To further confirm the effect of the Msx1 homeodomain on apoptosis, growth of cells transfected with Msx1 constructs as above was investigated using colony formation assays. The assays were done as described (Park et al. ibid) on the cells transfected as above. Briefly, the transfected cells were selected with 800 ug/ml of G418 for 2 weeks, and surviving colonies were stained with crystal violet. As shown in FIG. 4B, Msx1 lacking the homeodomain showed significant colony formation, whereas full length Msx1 dramatically inhibited colony formation. This result is in agreement with nuclear morphology data in FIG. 4A indicating that the homeodomain of Msx1 is not only involved in the interaction with p53, but is also responsible for the induction of apoptosis.

7-2 Stabilization of p53 by the Homeodomain of Msx1

HeLa cells were transfected with Msx1 vectors as in 7-1, and then whole cell lysates were prepared and used for Western blot analysis in Example 3 using anti-p53 antibody (SantaCruz), anti-GFP antibody (SantaCruz), and anti-beta-actin antibody (SantaCruz) to examine the steady state level of p53.

Figure 4C:
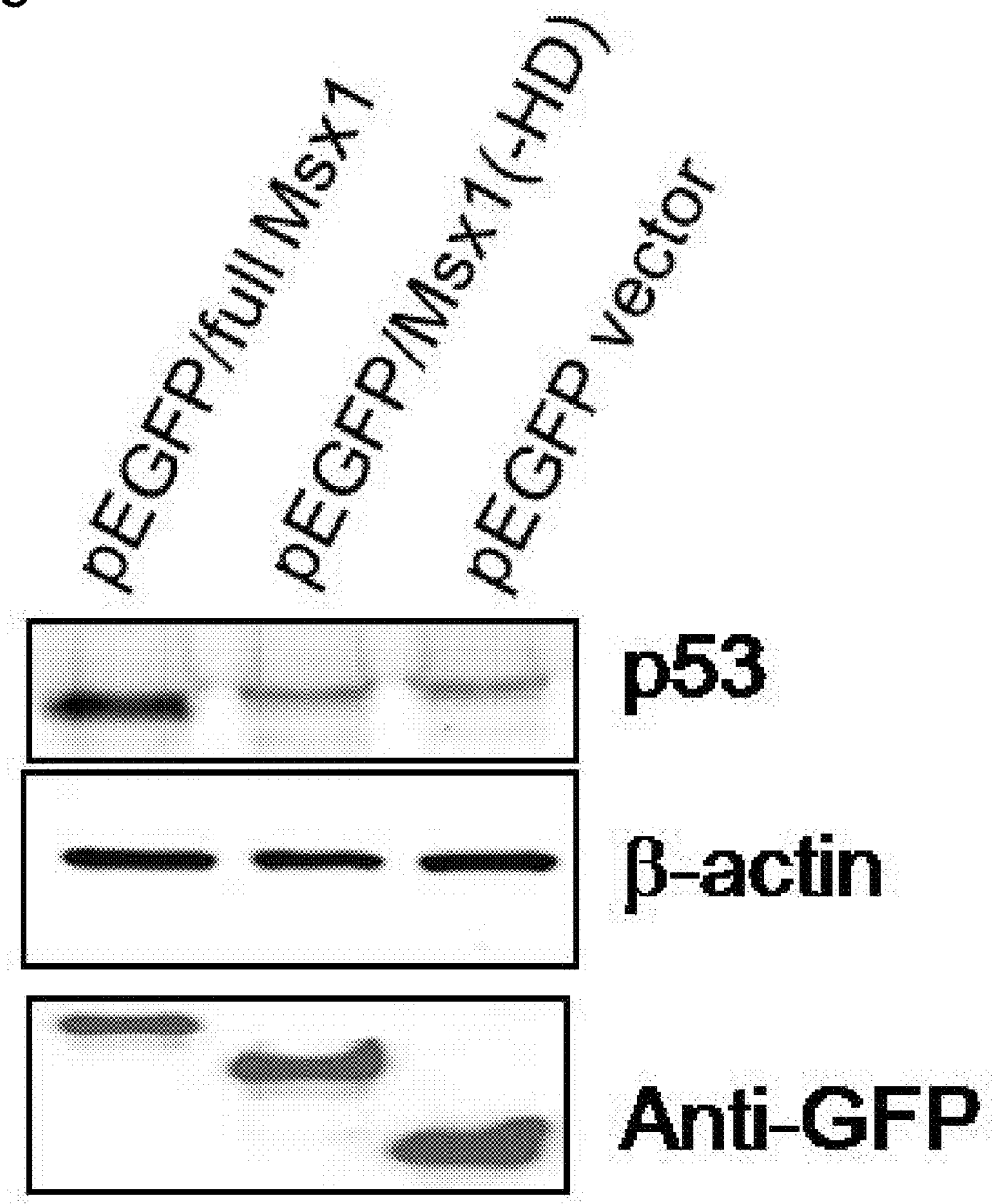
FIG. 4C shows the results of Western blot analysis showing that the homeodomain of Msx1 is necessary for inducing stabilization of p53 protein.

As shown in FIG. 4C, the steady state level of endogenous p53 was increased in cells transfected with full length Msx1, whereas no stabilization of p53 protein was observed in cells transfected with Msx1 lacking the homeodomain and with the control EGPF vector as is evident by the faint band intensity.

These results demonstrated that the homeodomain is as effective as full length Msx1 in inducing apoptosis through its interaction with p53.

Example 8

Stabilization of Exogenous p53 by Msx1

The stabilization activity of Msx1 on exogenous p53 was examined in p53-negative H1299 cells. The H1299 cells were cotransfected with pCMV-p53 and a fixed or increasing amount of pEGFP/full Msx1 vectors as in 7-1, and then the level of p53 was determined by Western blot analysis as in 7-2 using the same antibodies except that an anti-Msx1 antibody (BabCO, Berkley, Calif., USA) was used.

Figure 4D:
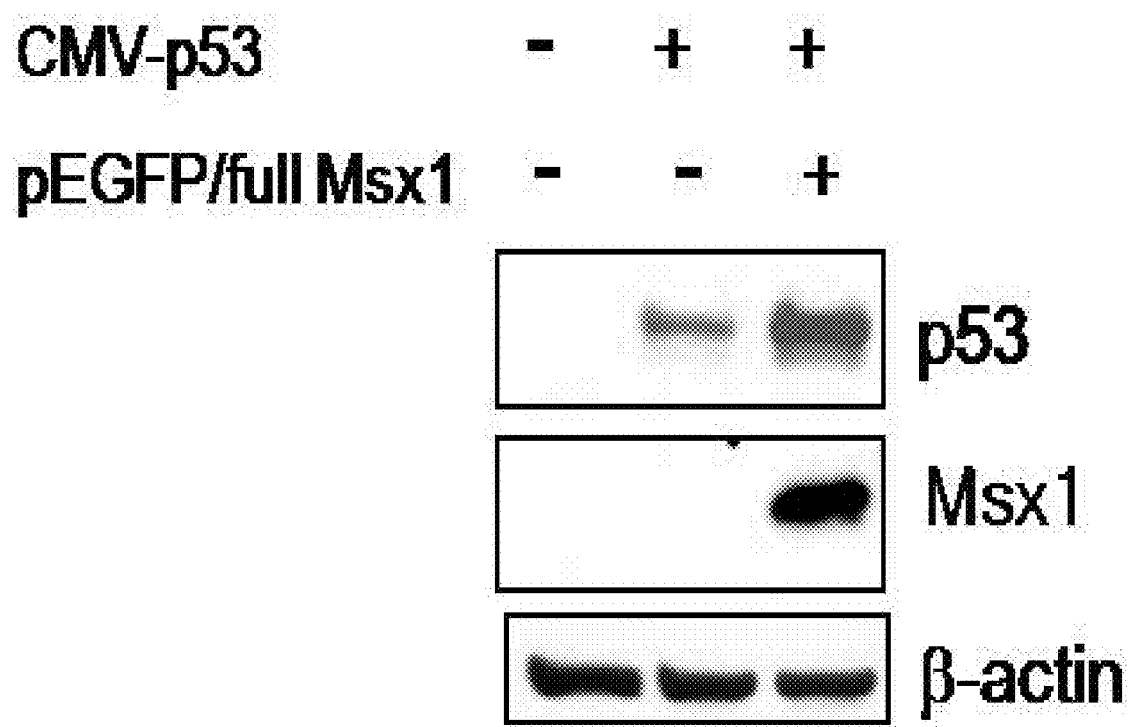
FIG. 4D shows the results of Western blot analysis showing that Msx1 is also able to stabilize the exogenous p53 in p53-negative H1299 cells where p53 proteins are exogenously introduced.
Figure 4E:
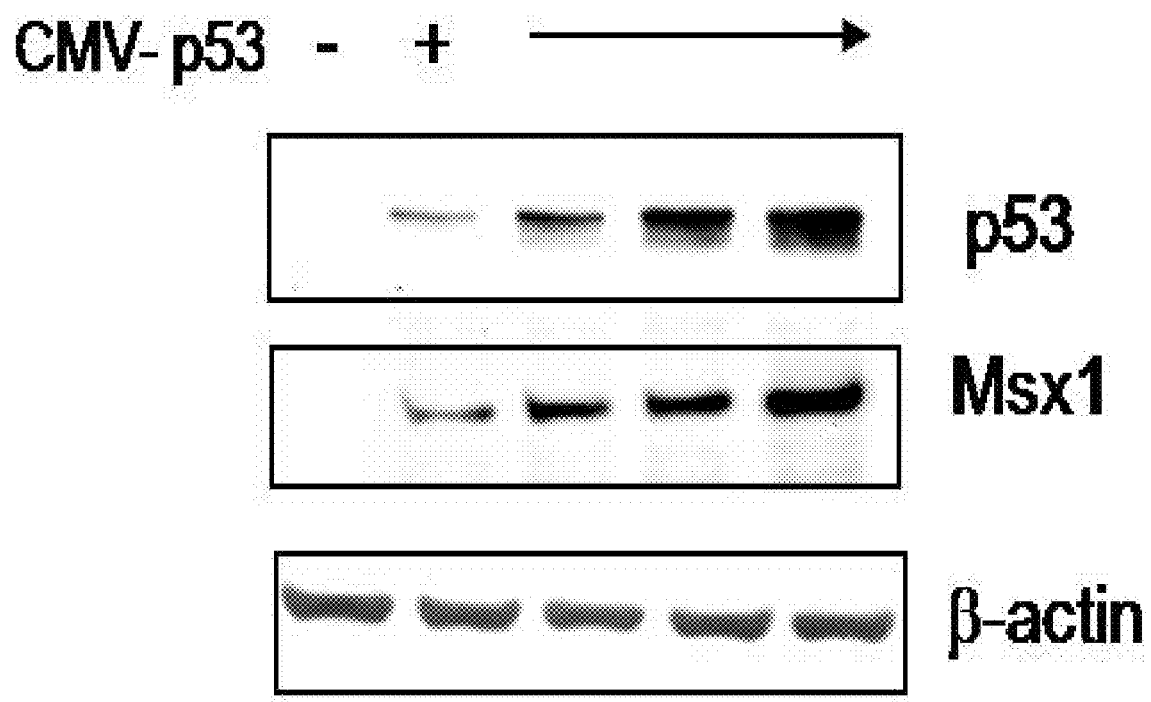
FIG. 4E shows the results of Western blot analysis showing the p53 stabilization is dependent on the intracellular concentration of Msx1.

As shown in FIG. 4D, coexpression of full length Msx1 stabilized exogenously expressed wild-type p53 protein compared with wild-type p53 alone, as indicated by the differences in the intensities of the bands. Further, as shown in FIG. 4E, transfection of H1299 cells with an increased amount of pEGFP/full Msx1 vectors showed that Msx1 was capable of stabilizing exogenous p53 in a concentration-dependent manner in p53 null human cancer cells.

These results indicate that the cells that not only have endogenous p53 but also that are lacking p53, particularly tumor cells, may equally be induced to undergo apoptosis by Msx1 in a concentration-dependent manner.

Example 9

Msx1 Suppresses Tumor Growth in Nude Mice 9-1 Establishment of subcutaneous (s.c) tumor model BALB/c mice purchased form Charles River Laboratories, Atsugi, Japan were used for an s.c. tumor model as described (Park et al., ibid). Briefly, $5 \times 10^6$ of exponentially growing HeLa cervical cancer carcinoma cells were injected subcutaneously into 5-week-old female BLAB/c mice in groups of 12 to 15. All the mice developed tumors within 10 days, and palpable tumors were detected within 2 weeks. Mice with tumors of a 100 $mm^3$ size were tested in an experiment described below.

9-2 Tumor Suppressing Activity of Msx1

Anticancer activity of Msx1 on s.c. tumors was tested as previously described (Park et al., ibid). Briefly, the s.c. tumor models prepared in 9-1 were injected with $5 \times 10^8$ pfu of Ad-Msx, Ad-mock, or Ad-p53 prepared as in Example 1. Ten animals were used for each group, and the mean tumor volume was determined by caliper measurements. The tumor volumes of mice treated as above were then measured every three days for 20 days after injection.

Figure 5A:
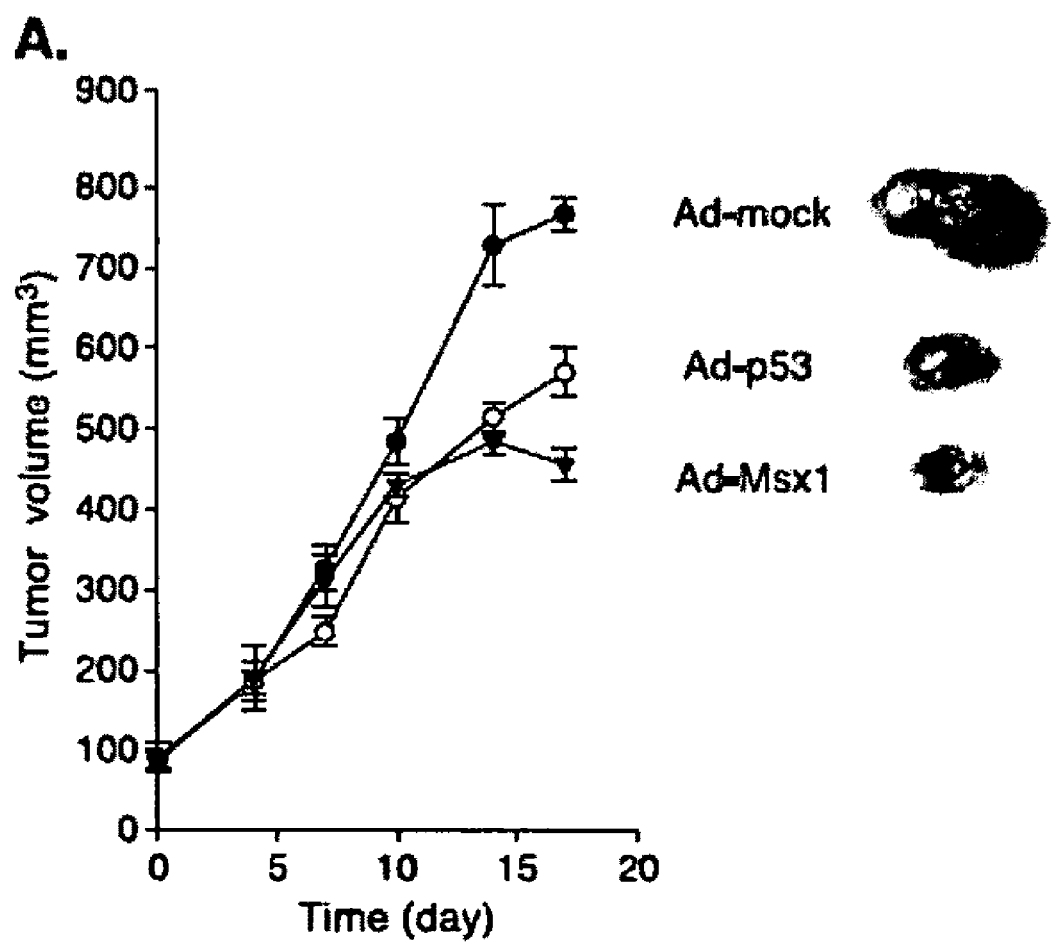
FIG. 5A is a graph showing that the intratumoral injection of Msx1 (Ad-Msx1) inhibits s.c. HeLa human cervical carcinoma growth as xenografts in nude mice (n=10). As negative and positive controls, an adenoviral vector without the Msx1 gene (Ad-mock) and with p53 (Ad-p53) were used, respectively.
Figure 5B:
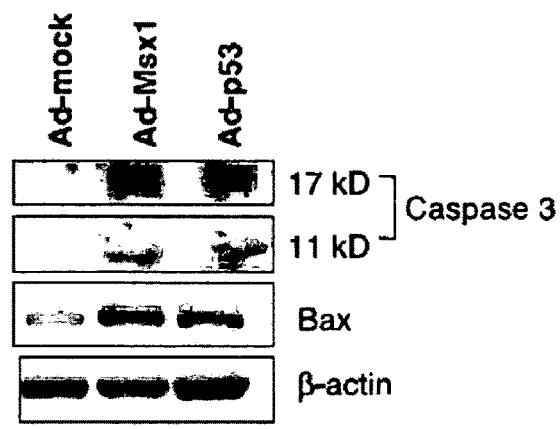
FIG. 5B shows the results of Western blot analysis showing the induction of apoptosis-related proteins, i.e., Caspase 3 and Bax in Ad-Msx1 treated tumors, and beta-actin was used as a control for an equal amount of protein loading.
Figure 5C:
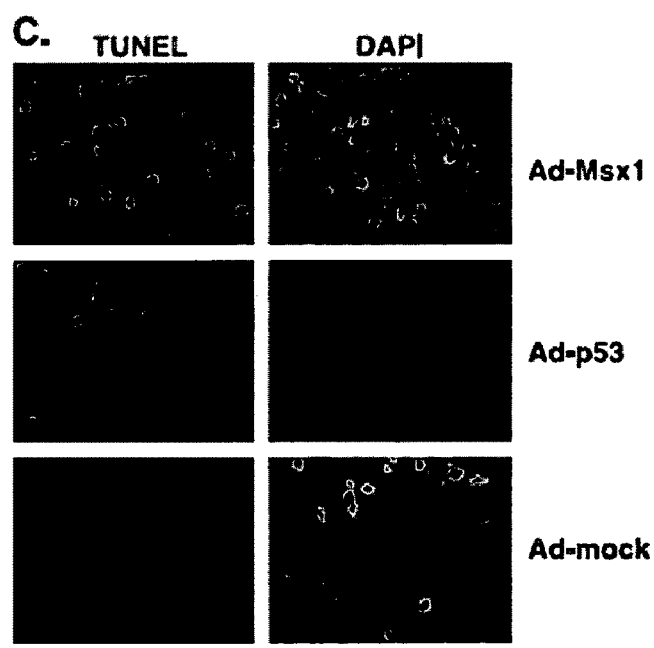
FIG. 5C shows the results of a TUNNEL assay using 8 μm frozen sections of tumor treated with each of Ad-Msx1, Ad-p53, and Ad-mock followed by a staining with DAPI to visualize nuclei. An increase in the number of apoptotic cells (green fluorescence) was detected in Ad-Msx1 as well as in Ad-p53 treated tumors.

FIGS. 5A to 5C illustrate the inhibitory activity of Msx1 on tumor growth in nude mice. As shown in FIG. 5A, there was no significant difference in tumor growth among different groups during the initial 4 days after adenovirus treatment. After 7 days, however, the Ad-Msx1-treated group began to show slowed tumor growth, whereas the Ad-p53 or Ad-mock treated group showed a continued increase in tumor size. At the time of sacrifice, about a 2-fold reduction in tumor seize was observed in the Ad-Msx1-treated group compared with the control Ad-mock treated group. The Ad-mock treated tumors were large, round, and highly vascularized, whereas the Ad-Msx1-treated tumors were small, collapsed, and pale in appearance (FIG. 5A, pictures in right side). Consistent with our results (Kim J et al., Cancer Gene Ther. 6: 172-8, 1999), Ad-p53 treatment effectively suppressed the growth of tumors.

To explore whether the suppression of tumor growth as above by Msx1 involved apoptosis, an immunoblot was performed on tumor tissue lysates with antibodies to proteins involved in apoptosis as described (Park et al., ibid). Antibodies used were anti-Caspase 3 (SantaCruz) and anti-Bax (SantaCruz). Further, the induction of apoptosis was confirmed by TUNEL assays (Park et al., ibid). The TUNEL assays were performed using an Apoptosis Detection System (Promega, Madison, Wis., USA) on 8 mm frozen sections from each tumor treated with adenovirus as above.

As shown in FIGS. 5B and 5C, expression of cell death-related proteins such as Caspase 3 and Bax was dramatically increased (FIG. 5B), and significantly more apoptotic cells were detected in Ad-Msx1 treated tumors (FIG. 5C).

These results demonstrate that Msx1 can be effectively used for the suppression of tumor growth by inducing apoptosis in vivo.

All the statistical analyses was determined by one-way ANOVA.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

---

What is claimed is:

1. A method of inducing apoptosis comprising a step of administering to a tissue or a subject associated with a disease condition selected from the group consisting of cervical cancer, ovarian cancer, and lung cancer, a therapeutically effective amount of Msx1 protein comprising SEQ ID NO:1 or comprising a homeodomain thereof, wherein the homeodomain consists of amino acid residues 239-298 of SEQ ID NO1.

2. The method of claim 1, wherein said induction of apoptosis involves direct interaction of Msx1 or homeodomain thereof with p53 protein.

3. The method of claim 2, wherein said interaction of Msx1 or the homeodomain thereof with p53 protein leads to increased stability, and/or nuclear localization of p53.

4. The method of claim 1, wherein said cancer contains p53 protein.

5. The method of claim 4, wherein said p53 protein is of endogenous or exogenous origin.

6. The method of claim 4, wherein said p53 is an inactivated protein.

7. A method of modulating p53 protein activity in a tissue or a subject comprising a step of administering to a tissue or a subject associated with a disease condition selected from the group consisting of cervical cancer, ovarian cancer, and lung cancer, a therapeutically effective amount of Msx1 protein comprising SEQ ID NO:1, or comprising a homeodomain thereof, wherein in the homeodomain consists of amino acid residues 239-298 of SEQ ID N01.

8. The method of claim 7, wherein p53 protein is of endogenous or exogenous origin.

9. The method of claim 8, wherein said modulation of p53 involves direct interaction of Msx1 or the homeodomain thereof.

10. The method of claim 9, wherein said interaction of Msx1 or the homeodomain thereof with p53 protein leads to increased stability, and/or nuclear localization of p53.

11. The method of claim 1, wherein the Msx1 protein is encoded by a nucleotide sequence comprising SEQ ID NO:2.

12. The method of claim 7, wherein the Msx1 protein is encoded by a nucleotide sequence comprising SEQ ID NO:2.

* * * * *